United States Patent
Weinberger

[11] Patent Number: 5,924,973
[45] Date of Patent: *Jul. 20, 1999

[54] METHOD OF TREATING A DISEASE PROCESS IN A LUMINAL STRUCTURE

[75] Inventor: Judah Z. Weinberger, Teaneck, N.J.

[73] Assignee: The Trustees of Columbia University in the City of New York, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/721,696

[22] Filed: Sep. 26, 1996

[51] Int. Cl.⁶ .......................................... A61N 5/00
[52] U.S. Cl. .................................. 600/3; 128/898
[58] Field of Search ....................... 128/898, 657; 600/1, 2, 3, 4, 5, 6, 7, 8, 434, 436; 606/108, 192, 194

[56] References Cited

U.S. PATENT DOCUMENTS

| | | | |
|---|---|---|---|
| 4,454,106 | 6/1984 | Gansow et al. | 600/3 |
| 4,824,659 | 4/1989 | Hawthorne | 600/4 |
| 4,889,707 | 12/1989 | Day et al. . | |
| 5,061,476 | 10/1991 | Simon et al. | 424/1.1 |
| 5,199,939 | 4/1993 | Dake et al. | 600/3 |
| 5,213,561 | 5/1993 | Weinstein et al. | 600/7 |
| 5,245,018 | 9/1993 | Kondo et al. . | |
| 5,300,281 | 4/1994 | McMillan et al. | 424/1.29 |
| 5,302,168 | 4/1994 | Hess | 600/3 |
| 5,320,824 | 6/1994 | Brodack et al. . | |
| 5,411,466 | 5/1995 | Hess | 600/3 |
| 5,436,352 | 7/1995 | Srinivasan et al. . | |
| 5,503,613 | 4/1996 | Weinberger | 600/3 |
| 5,556,389 | 9/1996 | Liprie | 604/264 |
| 5,616,114 | 4/1997 | Thorton et al. | 600/3 |

FOREIGN PATENT DOCUMENTS 9211032  7/1992  WIPO .

OTHER PUBLICATIONS

Bottcher et al., Int. J. Rad. Onc. Biol. Phys. 29(1):183–186 (1994) (Exhibit 6).

Brunner et al., Radiotracer Production pp. 220–229 (Exhibit 7).

Gellman et al., Circulation 84, Supple. 11, 46A–59A (1991) (Exhibit 8).

Guhlke et al., Technetium and Rhenium in Chemistry and Nuclear Medicine pp. 363–366 (1995) (Exhibit 9).

Hansen et al., Metal Based Drugs 2:105–110 (1995) (Exhibit 10).

(List continued on next page.)

*Primary Examiner*—Mickey Yu
*Assistant Examiner*—Kelly O'Hara
*Attorney, Agent, or Firm*—John P. White; Cooper & Dunham LLP

[57] ABSTRACT

An apparatus and a method of inhibiting a disease process in a luminal structure of a subject including introducing within the luminal structure a complex of a radionuclide and a chelating agent in an amount effective to inhibit the disease process.

25 Claims, 26 Drawing Sheets

OTHER PUBLICATIONS

Lever, Susan, Z., Radiotracer Production pp. 213–220 (Exhibit 11).

Mayberg et al., Rad. Res. 142(2):212–220 (1995) (Exhibit 12).

Order et al., Radiation Therapy of Benign Diseases (1990) (Exhibit 13).

Popowski et al., Int. J. Rad. Onc. Biol. Phys. 33(1):211–215 (1995) (Exhibit 14).

Prestwich et al., Med. Phys. 22(3):313–320 (1995) (Exhibit 15).

Rao et al., Inorganica Chimica Acta 180:63–67 (1991) (Exhibit 16).

Schwartz et al., J. Am. Col. Cardiol. 19(5):1106–1113 (1992) (Exhibit 17).

Shimotakahara et al., Stroke 25(2):424–428 (1994) (Exhibit 18).

Spencer R.P., Therapy in Nuclear Medicine pp. 3–15 (1978) (Exhibit 19).

Van Gog et al., J. Nucl. Med. 37(2):352–362 (1996) (Exhibit 20).

Verin et al., Circulation 92(8):2284–2290 (1995) (Exhibit 21).

Visser et al., J. Nucl. Med. 34(11):1953–1963 (1993) (Exhibit 22).

Waksman et al., Circulation 91(5):1533–1539 (1995) (Exhibit 23).

Waksman et al., Circulation 92(10):3025–3031 (1995) (Exhibit 24).

Waksman et al., Circulation 92(6):1383–1386 (1995) (Exhibit 25).

Wiedermann et al., J. Am. Col. Cardiol. 23(6):1491–1498 (1994) (Exhibit 26).

Wiedermann et al., Am. J. Phys. 267(1):H125–H132 (1994) (Exhibit 27).

Wiedermann et al., J. Am. Col. Cardiol. 25(6):1451–1456 (1995) (Exhibit 28); and.

Zamora et al., Int. J. Cancer 65:214–220 (1996) (Exhibit 29).

Schwartz et al. "Effect of external beam irradiation on neointimal hyperplasia after experimental coronary artery injury." JACC 19(5): 1106–13, Apr. 1992.

Visser et al. "Labeling of monoclonal antibodies with Rhenium–186 using the MAG3 chelate for radioimmunotherapy of cancer: a technical protocol." J Nucl Med 34:1953–63, Nov. 1993.

Waksman et al. "Endovascular low–dose irradiation inhibits neointima formation after coroanry artery balloon injury in swine." Circulation 91: 1533–9, Mar. 1995.

Waksman et al. "Intracoronary radiation before stent implantation inhibits neointima formation in stented coronary arteries." Circulation 92:1383–6, Sep. 1995.

Waksman et al. "Intracoronary low–dose beta–irradiation inhibits neointima formation after coronary artery balloon injury in the swine restenosis model." Circulation 92:3025–31, Nov. 1995.

Fig. 19

METHOD OF TREATING A DISEASE PROCESS IN A LUMINAL STRUCTURE

Within this application several publications are referenced by Arabic numerals within parentheses. Full citations for these references may be found at the end of the specification immediately preceding the claims. The disclosures of these publications in their entireties are hereby incorporated by reference into this application in order to more fully describe the state of the art to which this invention pertains.

BACKGROUND OF THE INVENTION

The present invention relates to an apparatus and a method to treat a disease process in a luminal structure. Such a structure includes, but is not limited to, a vein, artery, bypass graft prosthesis, the gastrointestinal (GI) tract, the biliary tract, the genitourinary (GU) tract, and the respiratory tract (e.g. the tracheobronchial tree).

Percutaneous transluminal coronary angioplasty (PTCA) is commonly used in the treatment of coronary artery obstruction, with over 400,000 procedures performed annually. PTCA is one of the most common current therapies for obstructive coronary artery disease (1). Unfortunately, it remains limited by a 30%–50% restenosis rate (2–5). The PTCA process involves the insertion of balloon catheters through the femoral artery to the targeted coronary artery. Injection of radio-opaque contrast into the proximal coronary artery allows fluoroscopic localization of stenosed coronary segments. Balloon catheters are advanced to the site of stenosis over extremely thin guide wires to position the catheter at the point of occlusion. The distal end of the catheter contains a balloon which is inflated for 2–4 minutes to the full diameter of the occluded artery, decreasing the blockage and improving blood flow.

In a related area, brachytherapy involves the implantation of a radioactive source within tissue to deliver localized radiation and is frequently applied to treat recurrent disease in an area previously treated by external beam radiation. Blind-end catheters may be used to deliver radiation to tumors in the esophagus, trachea, or rectum, for example. Advantages include the sparing of critical structures close to the tumor, and brevity of treatment (hours to days). Difficulties primarily involve anatomic constrains on implant placement. Common applications include the endoluminal treatment of recurrent endobronchial and bile duct tumors, the intracavitary treatment of cervical and endometrial cancer, and interstitial implants in unrespectable tumors with catheters or radioactive seeds.

As stated above, restenosis after arterial intervention in general, PTCA in particular, seem to be primarily due to medial smooth muscle cell proliferation. Conventional PTCA is performed using a balloon catheter such an over-the-wire type catheter manufactured, for example, by Scimed Life Systems, Inc, of Maple Grove, Minnesota or a mono-rail type catheter manufactured, for example, by Advanced Cardiovascular Systems, Inc, of Temecula, California. FIG. 1 depicts such a conventional over-the-wire balloon catheter 1. The conventional balloon catheter 1 is utilized in an angioplasty procedure as follows. A conventional guidewire 2 is inserted into the patient's artery until the distal end of the guidewire 2 is past a target area (not shown) of the artery (not shown) where there is a buildup of material. The conventional balloon catheter 1 has a lumen 3 running therethrough. The guidewire 2 is inserted into the distal end of the balloon catheter 1 and the balloon catheter 1 is advanced over the guidewire until the balloon section 1a of the balloon catheter 1 is adjacent the buildup of material. The balloon section 1a is then inflated by an inflation means (not show) connected to an inflation port 1b to clear the artery. Finally, the balloon section 1a is deflated, the balloon catheter 1 is pulled back up the guidewire and removed and the guidewire is likewise removed from the patient's artery.

The main concern associated with using balloon catheters is the possibility of balloon failure or rupture, and the resulting biological and radiological toxicity.

Approximately 40% of patients undergoing this procedure is have angiographic evidence of restenosis by 12 months. The mechanism of the restenosis process is not well understood, but both animal and human data suggest that it involves smooth muscle cell migration, proliferation, and neointima formation (6–9). Restenosis after stent implantation occurs at a somewhat lower rate of about 20%. Efforts to prevent restenosis using a variety of pharmacological or mechanical interventions or both have been largely unsuccessful in human and porcine models (10–19).

Although coronary artery blockage is a non-malignant disease, it has been suggested that treatment of the internal vessel walls with ionizing radiation could inhibit cell growth, and delay or even prevent restenosis (24, 36–40). There exists a long and extensive experience with the use of ionizing radiation to treat non-malignant disease such as aneurysmal bone cysts, arteriovenous malformations, arthritis, chondroma, heterotopic bone formation, total lymphoid irradiation (for renal and heart transplantation), and pterygium (reviewed in 28). Although this suggests that ionizing irradiation can be used to treat non-malignant, proliferative disorders, delivering such irradiation while minimizing damage to surrounding tissue has been a problem. And, in the case of balloon catheters, a continuous safety concern has been the rupture of the balloon and release of radioactive material into the bloodstream.

Details on catheters and their use can be found in U.S. Pat. No. 5,059,166, U.S. Pat. No. 5,213,561, U.S. Pat. No. 5,503,613, and PCT International Publication WO 95/19807. The disclosures of these documents in their entireties are hereby incorporated by reference into this application in order to more fully describe the state of the art to which this invention pertains.

SUMMARY OF THE INVENTION

The present invention provides a method of inhibiting a disease process in a luminal structure of a subject comprising introducing within the luminal structure a complex of a radionuclide and a chelating agent in an amount effective to inhibit the disease process.

This invention also provides an apparatus for treating a disease process in a luminal structure of a subject comprising a balloon catheter with a fluid delivery port connected thereto, and a radioactive fluid inserted into the balloon catheter through the fluid delivery port, said radioactive fluid comprising a complex of a radionuclide and a chelating agent in an amount effective to inhibit the disease process.

This invention further provides a method of treating a disease process in a luminal structure of a subject comprising introducing within the luminal structure the apparatus comprising a balloon catheter with a fluid delivery port connected thereto; and a radioactive fluid inserted into the balloon catheter through the fluid delivery port, said radioactive fluid comprising a complex of a radionuclide and a chelating agent in an amount effective to inhibit the disease process.

BRIEF DESCRIPTION OF THE DRAWINGS

FIG. 19 shows a shield according to an embodiment of the present invention;

DETAILED DESCRIPTION OF THE INVENTION

Figure 1:
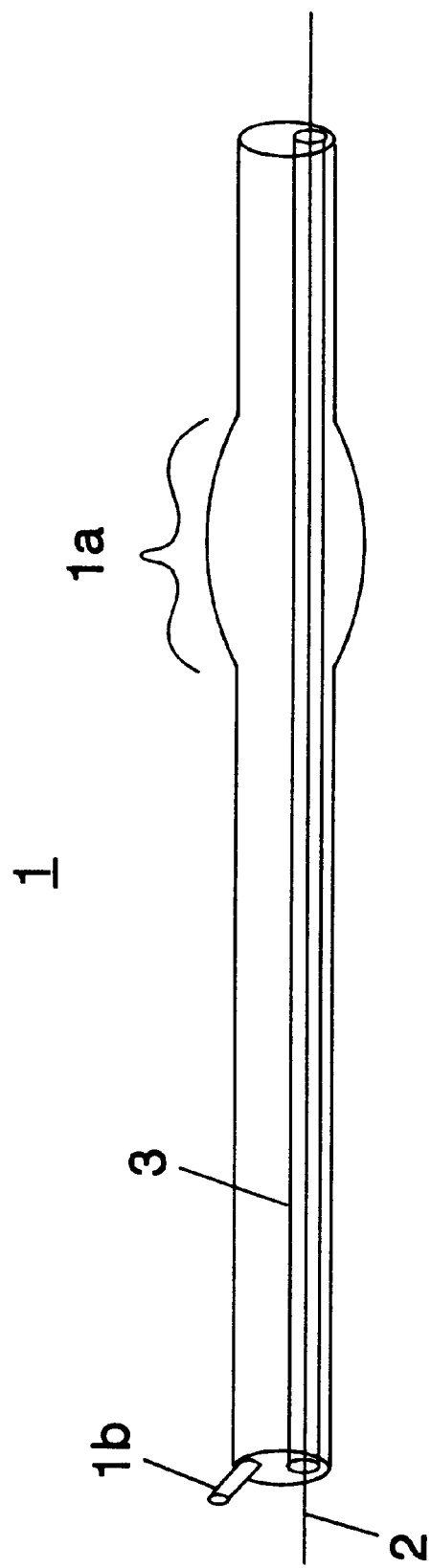
FIG. 1 shows the construction of a conventional over-the-rail type balloon catheter.

The present invention provides a method of inhibiting a disease process in a luminal structure of a subject comprising introducing within the luminal structure a complex of a radionuclide and a chelating agent in an amount effective to inhibit the disease process.

In one embodiment of the invention, the subject is a mammal.

In another embodiment of the invention, the subject is a human.

In yet another embodiment of the invention, the radionuclide is $^{188}$Re.

In another embodiment of the invention, wherein the chelating agent is $MAG_3$.

In yet another embodiment of the invention, wherein the complex is a $^{188}$Re-$MAG_3$ complex.

In another embodiment of the invention, the complex is introduced within the luminal structure within a catheter.

In yet another embodiment of the invention, wherein the catheter is a balloon catheter.

In another embodiment of the invention, the disease process is restenosis.

In yet another embodiment of the invention, the disease process is cell proliferation.

In another embodiment of the invention, the cell proliferation is associated with a endobronchial, bile duct, gastrointestinal, cervical, urinary bladder, or endometrial tumor.

In yet another embodiment of the invention, the luminal. structure is an artery.

In another embodiment of the invention, the luminal structure is a vein, a bypass graft prosthesis, a portion of the gastrointestinal tract, a portion of the biliary tract, a portion of the genitourinary tract, or a portion of the respiratory tract.

In yet another embodiment of the invention, said radionuclide is Na-24, Si-31, K-42, Sc-44, Co-55, Cu-61, Ga-66, Ga-68, Ga-72, Se-73, Sr-75, Br-76, Kr-77, Ge-77, Sr-90, Y-90, Tc-99, Tc-99m, Pd-103, In-110, Sb-122, I-125, Ho-166, Re-186, Ir-192, or Bi-212.

This invention further provides an apparatus for treating a disease process in a luminal structure of a subject comprising a balloon catheter with a fluid delivery port connected thereto, and a radioactive fluid inserted into the balloon catheter through the fluid delivery port, said radioactive fluid comprising a complex of a radionuclide and a chelating agent in an amount effective to inhibit the disease process.

In an embodiment of the invention, the radionuclide is $^{188}$Re .

In yet another embodiment of the invention, the radionuclide is Na-24, Si-31, K-42, Sc-44, Co-55, Cu-61, Ga-66, Ga-68, Ga-72, Se-73, Sr-75, Br-76, Kr-77, Ge-77, Sr-90, Y-90, Tc-99, Tc-99m, Pd-103, In-110, Sb-122, I-125, Ho-166, Re-186, Ir-192, or Bi-212.

In another embodiment of the invention, the chelating agent is $MAG_3$.

In a preferred embodiment of the invention, the complex is a $^{188}$Re-$MAG_3$ complex.

This invention also provides a method of treating a disease process in a luminal structure of a subject comprising introducing within the luminal structure the apparatus comprising a balloon catheter with a fluid delivery port connected thereto; and a radioactive fluid inserted into the balloon catheter through the fluid delivery port, said radioactive fluid comprising a complex of a radionuclide and a chelating agent in an amount effective to inhibit the disease process.

In an embodiment of the invention, the disease process is restenosis.

In another embodiment of the invention, the disease process is cell proliferation.

In yet another embodiment of the invention, the cell proliferation is associated with a endobronchial, bile duct, gastrointestinal, cervical, or endometrial tumor.

In another embodiment of the invention, the luminal structure is an artery.

In yet another embodiment of the invention, the luminal structure is a vein, a bypass graft prosthesis, a portion of the gastrointestinal tract, a portion of the biliary tract, a portion of the genitourinary tract, or a portion of the respiratory tract.

According to another aspect of the instant invention a dual-balloon catheter for treating a disease process in a luminal structure of a patient is provided, comprising an inner balloon, an outer balloon substantially concentric with and substantially surrounding the inner balloon, an inner balloon fluid delivery lumen in fluid connection with the inner balloon, and an outer balloon fluid delivery lumen in fluid connection with the outer balloon.

The dual-balloon catheter may further comprise a guidewire lumen connected to an outer surface of said outer balloon.

The inner lumen fluid delivery lumen, the outer lumen fluid delivery lumen, and the guidewire lumen may be in substantially axial alignment.

The dual-balloon catheter may further comprise a guidewire lumen extending through the outer balloon.

The inner lumen fluid delivery lumen, the outer lumen fluid delivery lumen, and the guidewire lumen may be in substantially axial alignment.

The dual-balloon catheter may further comprise a guidewire lumen extending through the outer lumen and the inner lumen.

The inner lumen fluid delivery lumen, the outer lumen fluid delivery lumen, and the guidewire lumen may be in substantially axial alignment.

The inner balloon may have a radiation producing coating. The outer balloon may have a radiation producing coating.

The interior surface of the outer balloon and/or an interior or exterior surface of the inner balloon may coated with a hydrogel for absorbing a fluid therein.

According to another aspect of the instant invention a method for treating a disease process in a luminal structure of a patient is provided, comprising inserting into the luminal structure a dual-balloon catheter including an inner balloon, an outer balloon substantially concentric with and substantially surrounding the inner balloon, an inner balloon fluid delivery lumen in fluid connection with the inner balloon, and an outer balloon fluid delivery lumen in fluid connection with the outer balloon, and inserting a radioactive fluid into at least one of the inner balloon and the outer balloon through the inner balloon fluid delivery lumen and the outer balloon fluid delivery lumen, respectively.

According to another aspect of the instant invention an indiflator for inserting fluid into a balloon catheter is provided, comprising an elongated tube for holding the fluid, the elongated tube having a first end and a second end, the first end of the elongated tube having a wall across the tube with a port therein for providing a fluid passage between an interior of the tube and an exterior of the tube, a plunger assembly including a plunger head with a first face and a second face and a plunger stem having first and second ends, the plunger head being adapted to slide within the tube and being connected to the first end of the plunger stem, lock means disposed at the second end of the tube for accepting and releasably locking the plunger stem, the second end of the plunger stem being disposed outside the tube, and a pressure valve disposed adjacent the second end of the plunger stem and being operatively connected to a pressure transducer on the second face of the plunger head facing the first end of the tube, whereby the pressure valve displays a pressure in an area of the tube between the first end of the tube and the second face of the plunger head.

The area of the tube between the first end of the tube and the second face of the plunger head may be substantially transparent and may be calibrated to indicate the volume between the first end of the tube and the second face of the plunger head. The calibration may be between about 1 and 5 cc's and is in increments of about 0.1 cc.

The radiation source may be any radiation emitting material. Specifically, the radiation source is a radionuclide, such as, for example, one from the group consisting of Na-24, Si-31, K-42, Sc-44, Co-55, Cu-61, Ga-66, Ga-68, Ga-72, Se-73, Sr-75, Br-76, Kr-77, Ge-77, Sr-90, Y-90, Tc-99, Tc-99m, Pd-103, In-110, Sb-122, I-125, Ho-166, Re-186, Re-188, Ir-192, Bi-212, or any other material selected from Tables 2–4, for example.

Regarding Tables 2–4, it is noted that the legend "A" refers to atomic mass, the half-life is given in years, days, hours, and minutes, where appropriate, a "Rad. Type" (radiation type) B+ indicates emission of a positron particle, B− indicates the emission of a beta particle, and G indicates the emission of a gamma photon.

The chelating agent may be selected from the group consisting of diethylenetriaminepentaacetic acid (DTPA), dimercaptosuccinic acid (DMSA), glucoheptonic acid (GH), mercaptoacetylglycylglycine (MAG$_3$), ethylenediaminetetraacetic acid (EDTA), N,N'-bis(mercaptoacetamido)-2,3-diaminopropanioc acid (CO$_2$-DADS) and related derivatives, N,N'-bis(mercaptoacetamido)ethylenediamine (DADS) and related derivatives, mono- and polyphosphonates, N,N'-bis(2-mercaptoethyl)ethylene-diamine (BAT) and related derivatives, ethylene hydroxy diphosphonate (ENDP), methylene diphosphonate (MDP), hydroxymethylenediphosphonate (HMDP), pyrophosphate (PYP), thiosemicarbazones, ethyl cysteinate dimers (L,L ECD and D,D ECD), hydroxyethyldiphoshonate (HEDP), ethylenediaminetetramethylphosphate (EDTMP), and any other which can coordinate a radionuclide or radioisotope.

The chelating agent binds the radionuclide thus forming a chelate or a complex. The chelating agent can be a bifunctional chelating agent, which chelates a metal and also conjugates to a receptor (i.e. a ligand). In some combinations, a radionuclide is chelated by more than one chelating agent, and a chelating agent may chelate more than one radionuclide.

A criteria for selecting the chelating agent includes the ease with which the chelating agent can be cleared from the subject's body in the event of balloon rupture.

Various complexes can be formed. By using the appropriate complex, it is possible to deliver the desired dosage of radiation while minimizing the impact of possible balloon rupture.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

The following are dosimetric calculations for various isotopes and source geometries in an attempt to identify the most suitable source designs for such treatments. An analysis of the excretion characteristics of certain complexes of radioisotopes and chelating agents is also included.

Methods and Materials

Analytical calculations are presented for dose distributions and dose rates for Ir-192, I-125, Pd-103, P-32, and Sr-90 as they might pertain to intracoronary radiations. The effects of source size and positioning accuracy are studied.

Results

Accurate source placement, dose rates >5Gray/minute, sharply defined treatment volume, and radiation safety are all of concern. Doses of 10–20 Gray are required to a length of 2–3 cm of vessel wall, which is 2–6 mm in diameter. The dose distribution must be confined to the region of the angioplasty, with reduced doses to normal vessels and myocardium. Beta particle or positron particle emitters have radiation safety advantages, but may not have suitable ranges for treating large diameter vessels. Gamma emitters deliver relatively large doses to surrounding normal tissues, and to staff. Low energy x-ray emitters such as I-125 and Pd-103 may represent a good compromise as might injecting a radioactive liquid directly into the angioplasty balloon.

Conclusions

Accurate source centering is found to be the single most important factor for intracoronary irradiations. If this can be accomplished then a high energy beta particle or positron particle emitter such as Sr-90 would be the ideal source. Otherwise the gamma emitter Ir-192 may prove optimum. A liquid beta particle or positron particle source such as P-32 has the optimum geometry, but may be unsafe for use with currently available balloon catheters when formulated as a bone-seeking phosphate.

Several groups have presented data demonstrating that 10–20 Gray of acute radiation delivered locally, via the temporary insertion of high activity gamma emitters at the time of angioplasty can inhibit restenosis in animal models (24,40). It has also been demonstrated that permanent radioactive coronary stents may be effective (52). Highly localized external beam therapy has been suggested as well (37,39). Most data to date have been obtained using animal models, but anecdotal reports suggest that radioactive treatment of human femoral arteries produces similar results (49). Preliminary human trials are being planned at several centers in the U.S. and Europe.

Preliminary studies have made use of currently available radioactive sources as none have been specifically designed for intracoronary treatments. Several manufacturers are considering modified High Dose Rate (HDR) afterloaders for this purpose. It therefore seems appropriate to identify the most suitable isotope and source design for such a device.

The design criteria are formidable. Doses of 10–20 Gray are required to a length of 2–3 cm of the vessel wall, which is 2–6 mm in diameter. The dose distribution should be tightly confined to the region of the angioplasty, with greatly reduced doses to normal vessels and the myocardia. Dose rates on the order of 5 Gray/minute are required in order to maintain treatment times within tolerable limits. This immediately suggests HDR afterloading, perhaps with specially designed sources suitable for insertion into standard or modified catheters.

Current angiographic techniques utilize open ended catheters which are flexible enough to be pushed through >100 cm of artery, and able to negotiate multiple bends between the femoral and coronary arteries. They must also pass through vessels as small as 3 mm diameter with small radii of curvature. The radioactive source must have similar flexibility. Source integrity is of great importance as dislodgement into a coronary artery could be fatal.

Most intraluminal studies to date have used Ir-192 seeds of 10–20 mCi activity. Typical seed dimensions are 0.5 mm diameter, 3 mm length (Best Industries, Springfield Va.). Multiple seed arrays are used with spacing 0.5 cm embedded in a 1 mm diameter plastic catheter. While these sources have proven useful for preliminary studies, the relatively high energy and low dose rates are not ideal. The need for specialized source and catheter design is obvious. For this reason, P-32, Sr-90, and other beta particle or positron particle emitters have been suggested.

Beta particle or positron particle emitters have obvious radiation safety advantages, useful for permitting treatments in the angiographic fluoroscopy suite. As we will show however beta particle or positron particle ranges may not be suitable for treating larger diameter vessels. Lower energy gamma and x-ray emitters such as I-125 and Pd-103 may represent a good compromise, but are not currently available at the required specific activities. Other possibilities include injecting a radioactive liquid directly into the angioplasty balloon.

We compare five isotopes for potential use in intracoronary irradiation: Ir-192, I-125, Pd-103, P-32, and Sr-90. While other suitable isotopes may exist, these five are all commercially available, although not necessarily in the form or activity required for intracoronary irradiation. They also represent the three main categories of possible isotopes, namely high energy gamma emitter, low energy gamma/x-ray emitter, and beta particle or positron particle emitter. The basic properties of each isotope are given in Table 1.

Ir-192 undergoes beta minus decay, but the therapeutically useful radiations are the 7 de-excitation gammas of the daughter nucleus Pt-192 which range in energy from 296–612 keV with an average energy of 375 keV. I-125 and Pd-103 both decay via electron capture with the therapeutically useful radiations being primarily characteristic x-rays from the daughter nuclei, Te-125 and Rh-109, respectively.

P-32 is a pure beta minus emitter which decays directly to the ground state of S-32 with a transition energy of 1.71 MeV. Sr-90 is a pure beta minus emitter with a half life of 28 years. It decays to Y-90, also a pure beta particle or positron particle emitter with a half life of 64 hours. The strontium and yttrium are in radioactive equilibrium, with the higher energy yttrium beta particle or positron particles (2.27 versus 0.54 MeV transition energy) providing most of the therapeutically useful radiation.

Given these basic isotopic properties, we consider a source consisting of a small metallic seed, similar to those currently used for conventional brachytherapy and HDR. Seeds would have dimensions on the order of $\leq 1$ mm diameter and 1–3 mm length. Treatment with such a source would require either multiple sources on a line (such as those currently available for conventional afterloading), or programmable source placement (similar to conventional HDR units) to permit treatment of 2–3 cm of vessel wall. The source could in theory be inserted directly into the coronary artery, or more likely, inserted into a conventional or slightly modified balloon catheter. In either case, as we will show later, it is highly desirable that the source be centered within the coronary artery to insure a uniform dose to the arterial walls.

To optimize source design we need to know the radial dose distribution, and the dose rate per mCi activity. The axial dose distribution is of less concern, as this can be optimized by suitably weighting the source dwell times as in conventional HDR. We assume that for each of the isotopes listed in Table 1, a suitable source can be fabricated. For comparison purposes only we consider first a single source of 0.65 mm diameter and 5 mm length, with the axial position programmable to enable treatment of any length of arterial wall.

For gamma and x-ray emitters the radial dose distributions from point or line sources are well known on theoretical considerations. Many measurements have been reported as well, although measurements at distances less than several millimeters are difficult due to technical con siderations. AAPM Task Group-43 (TG-43) (51) has reviewed the available data and presented recommendations for calculating dose:

$$\text{Dose}(r,\Theta) = S * \lceil * G(r,\Theta) * g(r) * F(r,\Theta) \qquad \text{Eq. 1}$$

where:

S=air kerma strength

⌈=dose rate constant r=radial distance from source

Θ=angle from point of interest to center of source, as measured from the axial dimension of the source (we consider here Θ=90°

G="geometry factor" resulting from spatial distribution of the radioactivity within the source. For a 3 mm long line source, $G(r,\Theta) \cong r^{-2}$ for $\Theta \cong 90°$ g=radial dose function, given as $$\sum_i a_i * r^i,$$

where:

$a_i$=fitted parameters to a fifth order polynomial

F=anisotropy factor describing dose variation versus angle. This function is normalized to unity at Θ=90°

In practice, for distances <1cm and Θ≅90° all of the correction factors in Equation 1 are approximately unity as photon attenuation and photon scatter very nearly cancel. Williamson and Zi (53) have shown that for the Ir-192 sources currently used in HDR units radial errors (for r<1 cm) are <1%, and anisotropy errors (for 30°<Θ<150°) are <10%. Dose versus distance thus approximates the $1/r^2$ law except for the lowest energy x-ray sources. Specific details on all factors in Equation 1, as well as values for S, ⌈, $a_i$, G, g, and F are found in TG-43 (51).

For beta minus emitters dose versus radial distance from a point source can be calculated more directly using the equation:

$$\text{Dose}(r) = \int_{E=0}^{Emax} F(E) * A * k * S(E') * \rho * dE / 4\Pi r^2 \qquad \text{Eq. 2}$$

where:

r=distance in cm

F(E)=initial fluence of electrons with energy E

A=activity in mCi k=conversion factor from MeV-mCi/gm to Gy/min

S(E')=mean restricted stopping power for electron of energy E' in MeV/cm

E'=energy of electron with initial energy E at distance r from the source

ρ=density

Electron ranges and stopping powers were taken from Berger and Seltzer (44). F(E) spectra for P-32 and Sr-90 (in equilibrium with Y-90) were obtained from the literature (45,43).

The radial dose distributions given by Equations 1 and 2 were integrated over the axial length (L) of the source to properly correct for the distance "r", and for Equation 1 the anisotropy factors. Thus at a radial distance "r" from a source of axial length "L":

$$\text{Dose}(r) = \int_{X=-L/2}^{+L/2} \text{Dose}(\text{Sqr. Root}(r^2 + x^2))dx \qquad \text{Eq. 3}$$

where:

Dose (r) is given either by Equation 1 or 2.

For beta particle or positron particle sources it was assumed that the radioactive isotope was plated on the exterior surface of the seed, and that electron range was insufficient to pass through the seed. Thus, for each radial position, Equation 2 was integrated only over the solid angle of the source which is "visible" at a distance "r". For x and gamma sources internal absorption is implicitly included in the factor F(r,Θ). Absolute dose rates in water per mCi activity were also calculated directly from Equations 1–3.

Figure 11:
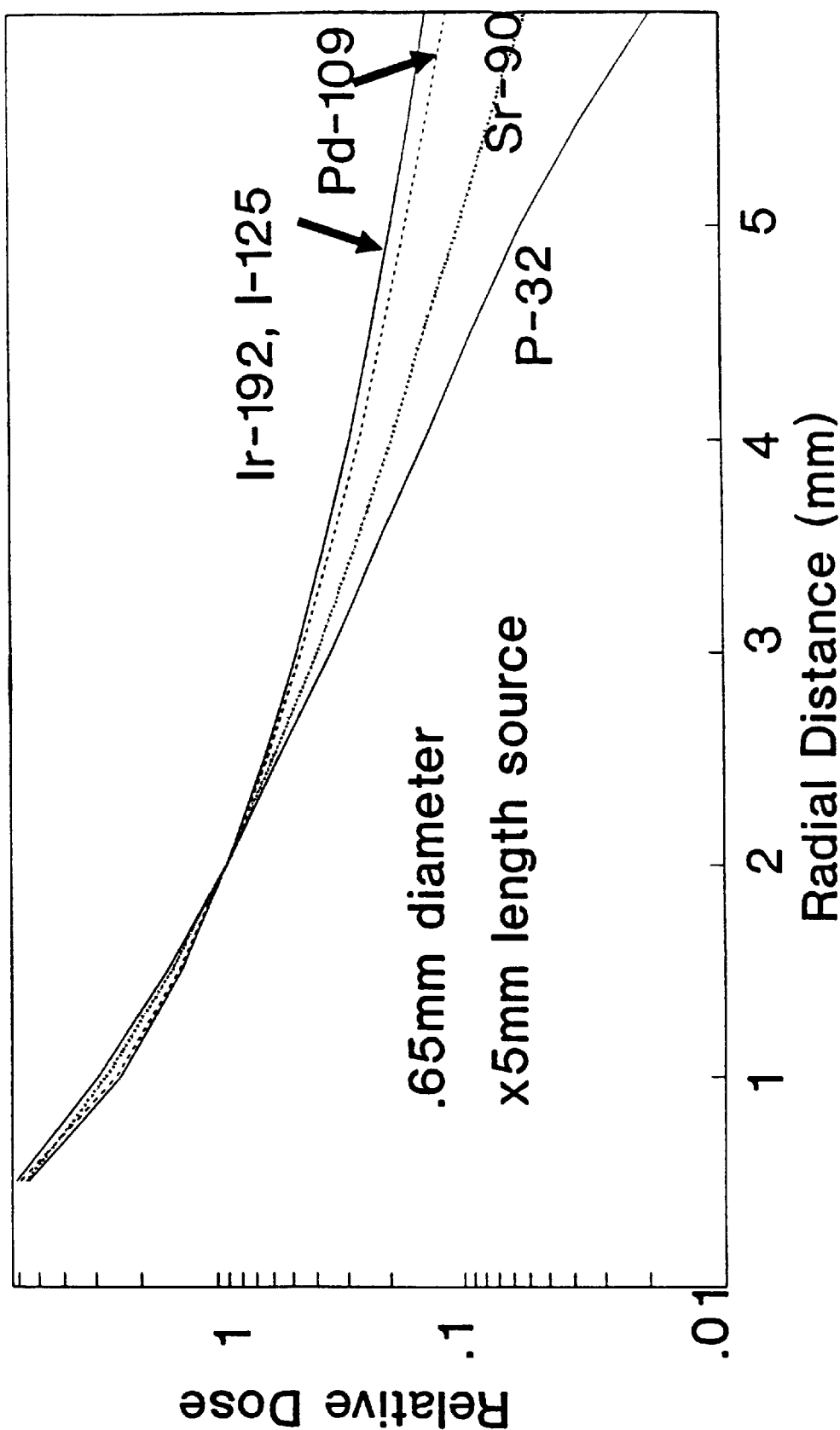
FIG. 11 shows dose versus distance for Ir-192, I-125, Pd-103, P-32, and Sr-90.

FIG. 11 presents relative dose versus radial distance for a source of 0.65 mm diameter, and 5 mm length, for each isotope. Doses are normalized to 1.00 at a distance of 2 mm, the approximate radius of a typical coronary artery.

Ir-192 and I-125 have nearly identical dose distributions, with both being very nearly equal to inverse square falloff of dose. Pd-103, because of its lower photon energy has a more rapid dose fall off, as attenuation becomes significant even at small distances.

The beta particle or positron particle emitters P-32 and Sr-90 show even more rapid dose fall off versus distance because of the large number of low energy electrons in their respective spectra which have concomitant short ranges. P-32, with a maximum energy of 1.7 MeV and mean energy of 0.690 MeV (versus 2.27 and 0.970 MeV for Sr-90/Y-90) has the greatest dose fall off.

Source activities required to achieve a dose rate of 5 Gray/minute at a radial distance of 2 mm to a 2 cm length of arterial wall are given in Table 1. This equates to a 4 minute treatment time to deliver 20 Gray, varying with the diameter and axial extension of the treatment volume. As seen in Table 1, suitable X and gamma sources require activities ≧1Ci, whereas beta particle or positron particle sources require only tens of mCi. Due to uncertainties in ⌈ factors, source anisotropy, and dose variation at distances <0.5 cm the values given in Table 1 for required activity should be considered approximate.

Iridium (Best Industries, Springfield, Va.), Phosphorus (Mallinckrodt, Inc., Technical Product Data. St. Louis, Mo.), and Strontium (New England Nuclear, Boston Mass.) sources of suitable size and activity can readily be fabricated, although not all are currently commercially available. Iodine and Palladium on the other hand present technical problems in fabrication at this time.

Although the effect is more dramatic for beta particle or positron particle sources, FIG. 11 shows that even gamma sources have extremely rapid dose fall off with radial distance. Dose uniformity is thus critically dependent on centering the source with the artery.

Figure 12:
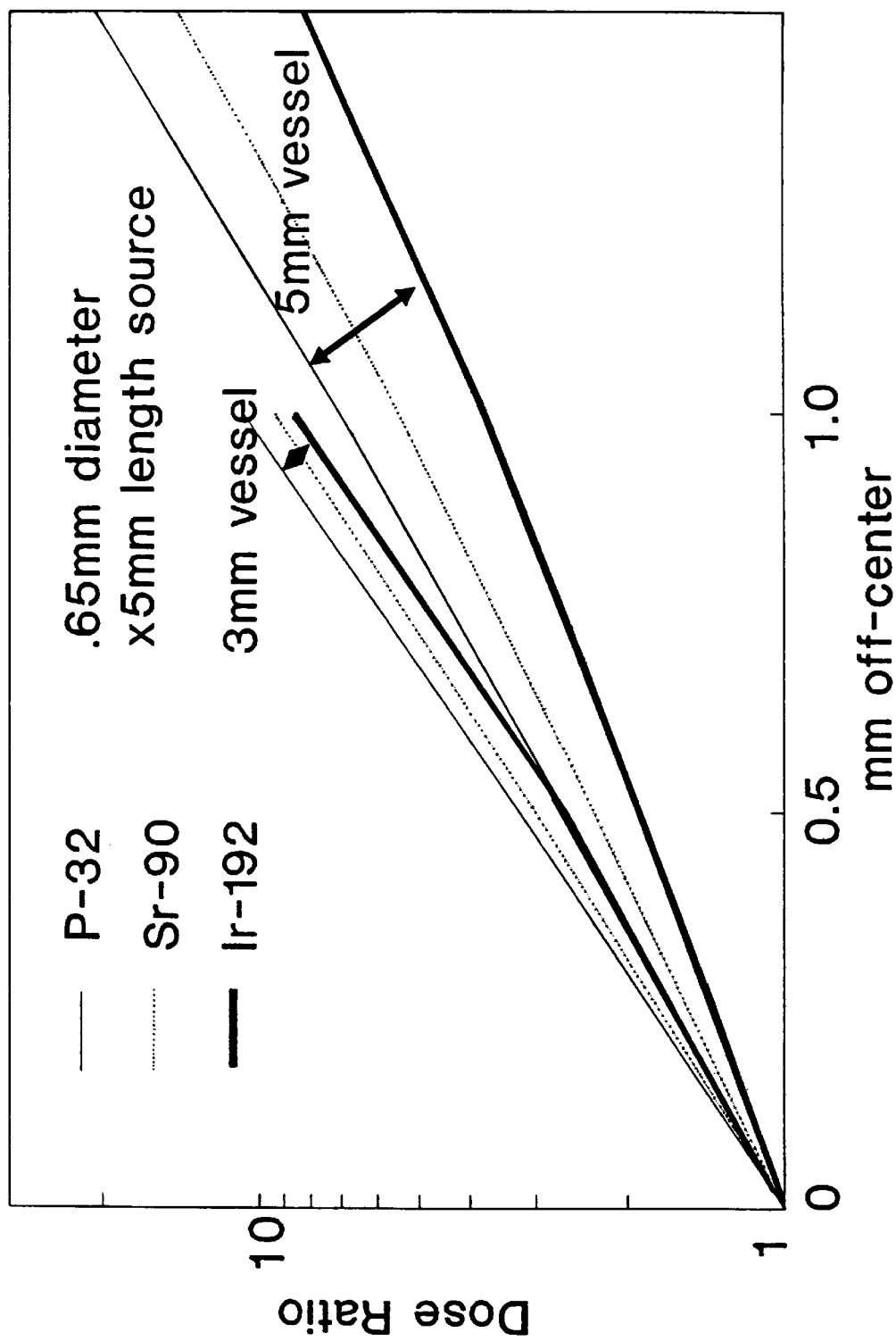
FIG. 12 shows dose asymmetry (defined as maximum/ minimum dose to vessel wall) resulting from inaccurate centering of 5 mm long P-32, Sr-90, or Ir-192 sources within arteries of 3 and 5 mm diameter.

Dose asymmetry can be calculated from FIG. 11, and in FIG. 12 we demonstrate the magnitude of this asymmetry resulting from inaccurate centering of a single 5 mm long source of Sr-90, P-32, or Ir-192. Plotted are the ratios of maximum vessel dose to minimum vessel dose in vessels of 3 and 5 mm diameter as a function of centering error. As seen, centering errors as small as 0.5 mm in a 5 mm diameter vessel result in dose asymmetries ranging from 2.25 for Ir-192 to 2.62 for P-32. This corresponds to deviations from "prescription dose" of +56% and −31% for Ir-192, and +60% and −30% for P-32. Expectedly, the magnitude of the dose asymmetry increases as source energy decreases. Ir-192 thus yields the smallest dose asymmetries, and P-32 the largest.

Figure 13:
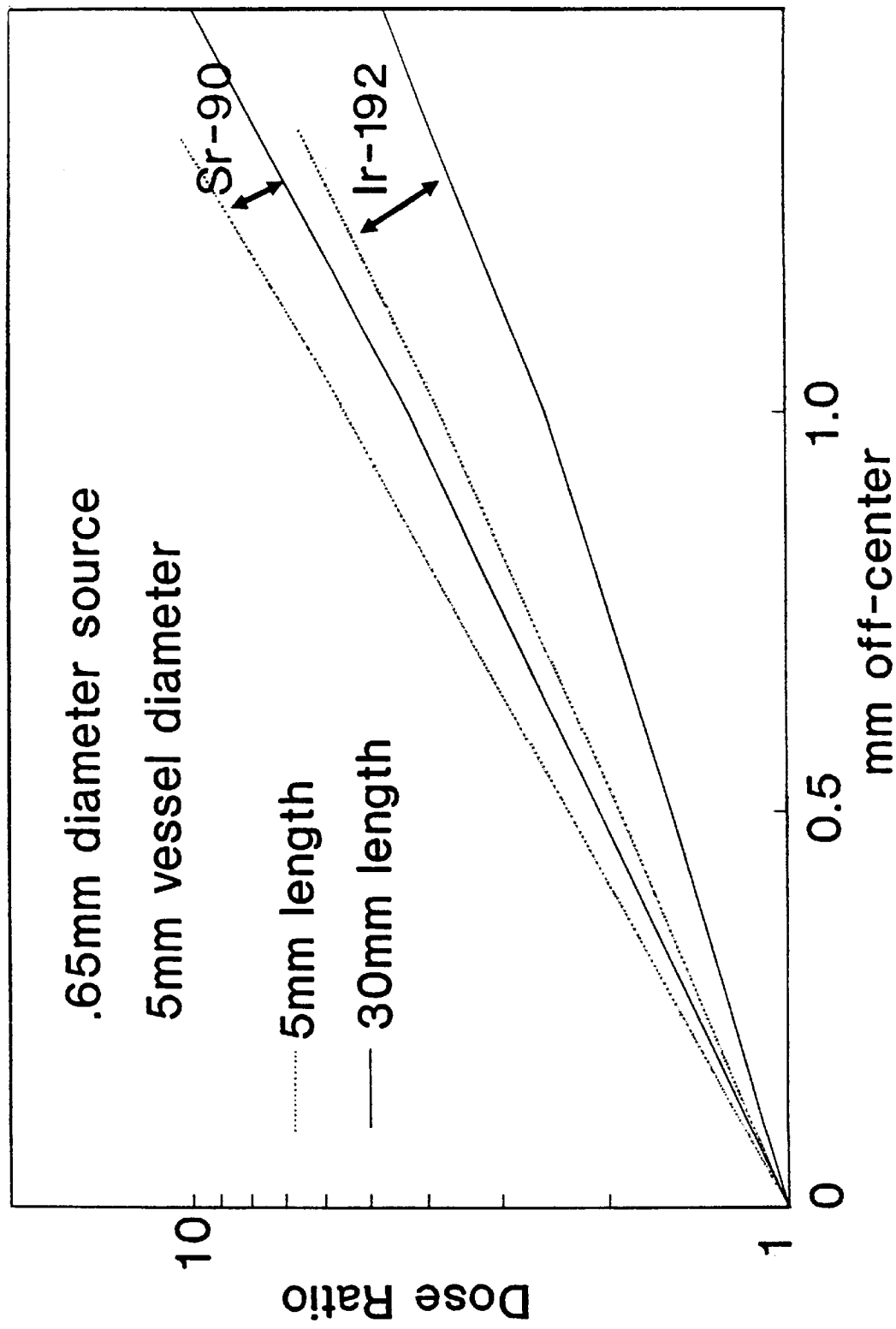
FIG. 13 shows a comparison of dose asymmetry for Sr-90 and Ir-192 sources of 5 and 30 mm length in a 3 mm diameter vessel.

If source position is programmed to treat a longer length of vessel wall dose asymmetries are slightly reduced because dose fall off versus radial distance is less rapid for a line source as compared to a point source. Accurate source positioning is still of major importance however, as FIG. 13 shows significant asymmetries even for a 3 cm long treatment volume in a 5 mm diameter vessel.

Figure 14:
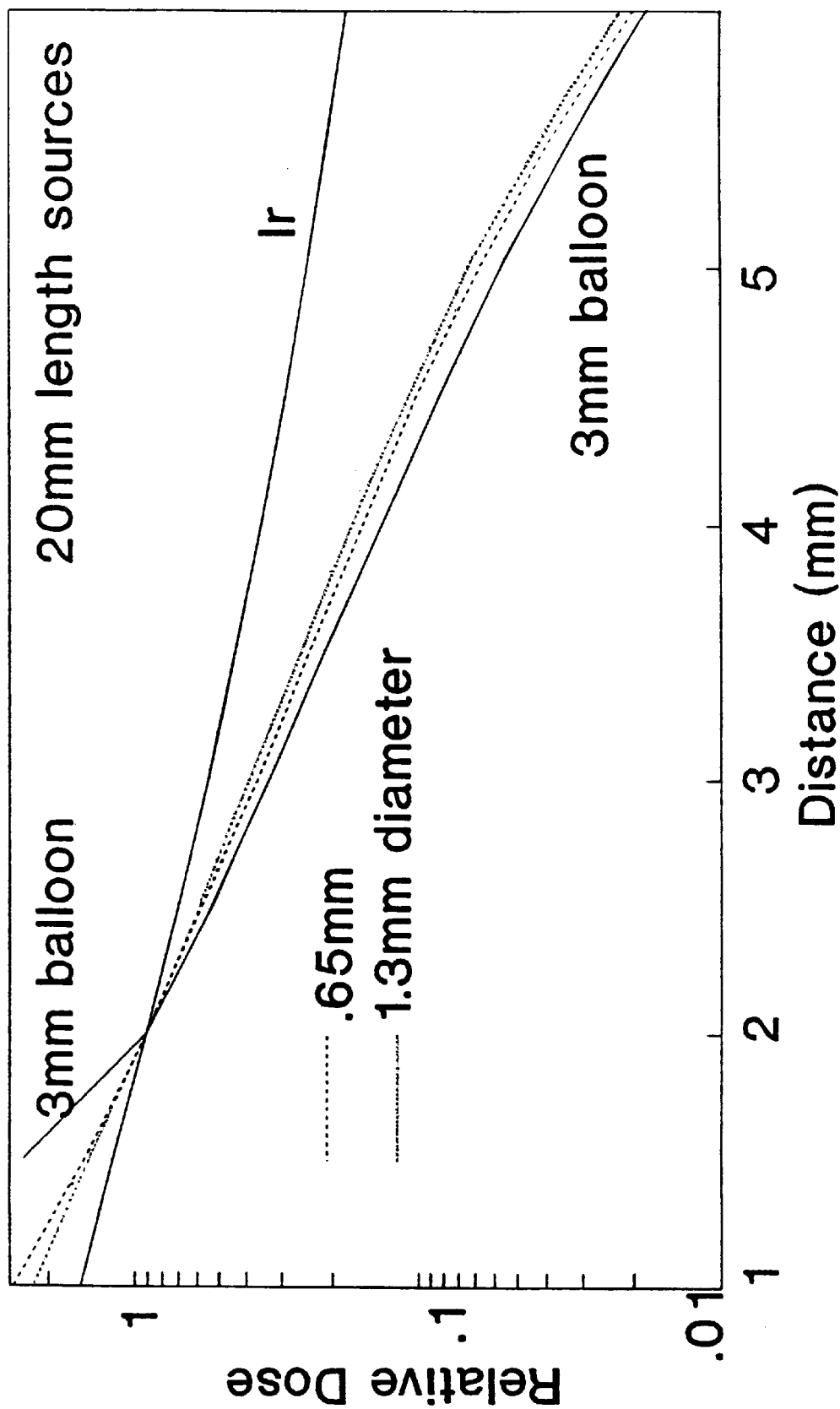
FIG. 14 shows radial dose distribution for P-32 wires of 0.65 and 1.3 mm diameter, and for a 3 mm diameter P-32 balloon.

For any source the radial dose distribution (and subsequent error resulting from inaccurate source positioning) can be slightly improved by increasing the source thickness, but this has obvious limitations in terms of source flexibility. FIG. 14 shows that for treatment of a 2 cm length of vessel increasing the diameter of a P-32 source from 0.65 to 1.3 mm results in a marginal improvement in dose distribution. Thus, for all sources a minimum size is optimum.

The dosimetric asymmetry introduced by errors in source positioning can be eliminated if we consider the possibility of using a liquid beta particle or positron particle emitter such as P-32 sodium phosphate solution, which could be injected directly into the angioplasty balloon, or even coated onto its inner surface. Balloons are normally inflated with contrast, but they could, in principle, be inflated with P-32 solution. This would have the distinct advantage of guaranteeing that the radioactive source is in the correct position, and in direct contact with the vessel walls, thus optimizing dose uniformity.

A typical balloon is 2–3 cm in length (l), and is inflated to the full diameter (d) of the vessel. Depending on the degree of arterial occlusion, a 2 cm long balloon inflated to a diameter of 3 mm would have a total volume of approximately 0.14 ml (i.e., volume=$IId^2l/4$). The resulting radial dose distribution of the balloon can be calculated using a slightly modified formulation of Equations 2 and 3, where the integration is extended over the radial extent of the source. The equations describing this have been given in reference (52). The resulting dose distribution is similar to that of P-32 coated seed or wire, as shown in FIG. 14, which compares doses for 20 mm length wires and a balloon.

A dose rate of 5 Gray per minute could be achieved from a balloon filled with a solution of approximately 50 mCi/ml specific activity. The catheter running from the femoral to the coronary artery would also be filled with radioactive solution, but since the diameter of this tube is $\leq 0.4$ mm (Medtronic Inc., Deerfield Beach, Fla.), the dose rate to normal vessels around this tube would be less than 20% of the treatment dose, depending on the diameter of the vessels. A 20 Gray treatment would result in less than 4Gray to normal vessel—well below normal tissue tolerance.

We are thus left with a choice between high energy gamma or beta particle or positron particle emitters. The desired criteria for a source are: high dose rate per mCi; high specific activity; long half life; and treatment distance of at least 3–4 mm.

No available isotope is ideal. Sr-90 has advantages in terms of specific activity, dose rate, radiation safety, and half life; while Ir-192 has an advantage in terms of radial dose distribution. Both isotopes could be fabricated at the required specific activities using current technology.

There is a trade off between the increased radial range of Ir-192, and the safety advantages of Sr-90. Although it is a qualitative assessment, it appears from FIG. 11 that if the radial treatment distance was always $\leq 1.5$ mm, Sr-90 would be the isotope of choice. For larger treatment distances, Ir-192 would be better.

The argument however hinges on one's ability to center the radioactive source in the artery. If ideal centering were possible then any source would provide radial dose homogeneity and Sr-90 would be the isotope of choice. Current catheter design however dose not guarantee centering, and the increased range of Iridium could be of advantage.

Based upon dose distributions, dose rate, specific activity, and commercial feasibility both Ir-192 and Sr-90 could be suitable sources for intracoronary irradiation. Higher energy beta particle or positron particle sources would be highly desirable, but these invariably have extremely short half lives. We have shown here that P-32, with a transition energy of 1.7 MeV is marginally acceptable as a possible source, so one can rule out any isotopes with lower transition energies.

Isotopes with shorter half lives (14 days for P-32) would also prove to be impractical.

On the other end of the beta particle or positron particle spectrum, there are no isotopes with half lives greater than Sr-90 (28 years) that also have a greater transition energy (2.27 MeV for Sr-90 's daughter Y-90). This seems to make Sr-90 the beta isotope of choice, although other possibilities exist, such as Sb-124 with a half life of 60 days and average energy of 918 keV. Dose distributions for other beta particle or positron particle isotopes are similar to those shown in FIG. 11, and development of such sources would not alter our basic conclusions.

The introduction of P-32 solution directly into the angioplasty balloon is particularly attractive in that it eliminates all problems of dose inhomogeneity and range. With current technology catheters however there is a 1–2% occurrence of balloon failure. If the balloon and 100 cm length of catheter were completely filled with P-32 solution, and if the balloon failed, there could then be as much as 15 mCi of P-32 released directly into the blood. Since P-32 as the phosphate moiety is a bone seeking isotope (occasionally used for the treatment of polycythemia vera), this could result in a skeletal dose >9.5 Gy, and a whole body dose >1.5 $Gy^2$ (50)—both unacceptable risks. Alternatively, other chemical forms of P-32, more rapidly cleared, would not home to the bone marrow and therefore have an acceptable toxicity profile. Still, the dosimetric advantages of such a treatment seem to warrant further studies of catheter design. Another possible solution to this problem would be to identify a beta particle or positron particle emitter whose chemical formulation would be more benign and have shorter biological half lives. Such radioactive solutions may be selected from the group consisting of fluids containing Cu-61, Se-73, Co-55, Sc-44, Sr-75, Kr-77, Ga-68, In-110, Br-76, Ga-66, Ga-72, Sb-122, Na-24, Si-31, Ge-77, Ho-166, Re-188, Bi-212, Y-90, K-42, Ir-192, I-125, Pd-103, Sr-90, and radioactive sodium-chloride, or any other chemical compound formulated from the isotopes given in Table 3, for example.

At current prices, Ir-192, Sr-90, and P-32 sources of the required activities could all be fabricated for approximately $10^3$–$10^4$, not counting development costs. Sr-90 has by far the longest half life (28 years), with Ir-192 (74 days) and I-125 (60 days) lagging far behind. Cost may therefore be a significant factor in source selection.

Figure Captions

11. Radial dose versus distance for Ir-192, I-125, Pd-103, P-32, and Sr-90. Sources are 0.65 mm diameter and 5.0 mm length. Doses have been normalized to 1.0 at a radial treatment distance of 2.0 mm.
12. Dose asymmetry (defined as maximum/minimum dose to vessel wall) resulting from inaccurate centering of 5 mm long P-32, Sr-90, or Ir-192 sources within arteries of 3 and 5 mm diameter. When the source is centered in the artery, the dose asymmetry is 1.0.
13. comparison of dose asymmetry for Sr-90 and Ir-192 sources of 5 and 30 mm length in a 5 mm diameter vessel. When the source is centered in the artery, the dose asymmetry is 1.0.
14. Radial dose distribution for P-32 wires of 0.65 and 1.3 mm diameter, and for a 3 mm diameter P-32 balloon. All sources are 20 mm length. The dose for a 20 mm length Ir-192 source is shown for comparison. Doses have been normalized to 1.0 at a radial treatment distance of 2.0 mm.

Figure 2:
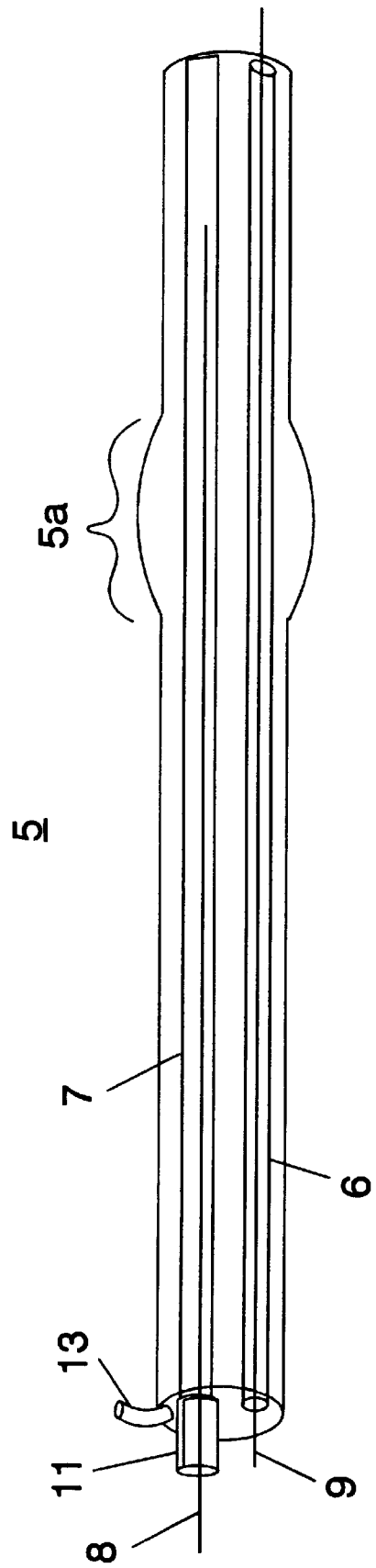
FIG. 2, shows the construction of a balloon catheter according to a first embodiment of the present invention.

Referring now to the Figures, FIG. 2 shows a balloon catheter according to a first embodiment of the present invention, which can be used to perform the method according to the present invention. The apparatus is particularly suited for delivering radioactive doses to the coronary artery. The preferred embodiment will be described with reference to the coronary artery, but this is by way of example, and not limitation, as the present invention may also be used to deliver radiation to other luminal structures.

The apparatus comprises a balloon catheter 5 with a guidewire lumen 6 extending entirely through the balloon catheter 5 and a blind lumen 7 which is closed at the distal end of the balloon catheter 5, for receiving a radiation dose delivery wire 8. The guidewire lumen 6 is sized to fit around a guidewire 9 and to allow the guidewire 9 to slide therein. The length of guidewire 9 is sufficient to allow it to extend past a target segment of the artery and it may be, for example, greater than about 110 cm for use in the coronary artery. For use in other arteries, the length of guidewire 9 may also be greater than about 110 cm or it may be less.

The outside diameters of the guidewire 9 and the radiation dose delivery wire 8 may be about 0.014 inch and in this case the inside diameters of the guidewire lumen 6 and the blind lumen 7 are slightly larger, to permit movement of the balloon catheter 5 over the guidewire 9 and movement of the radiation dose delivery wire 8 through blind lumen 7.

The radiation dose delivery wire entry port 11, at the proximal end of the balloon catheter 5, is adapted to receive the radiation dose delivery wire 8 and to provide a watertight seal. Thus, the radiation dose delivery wire 8 is isolated from contact with the patient's body fluids. The balloon inflation port 13 allows inflation of the balloon section 5a at the distal end of the balloon catheter 5 in the conventional manner.

Figure 3:
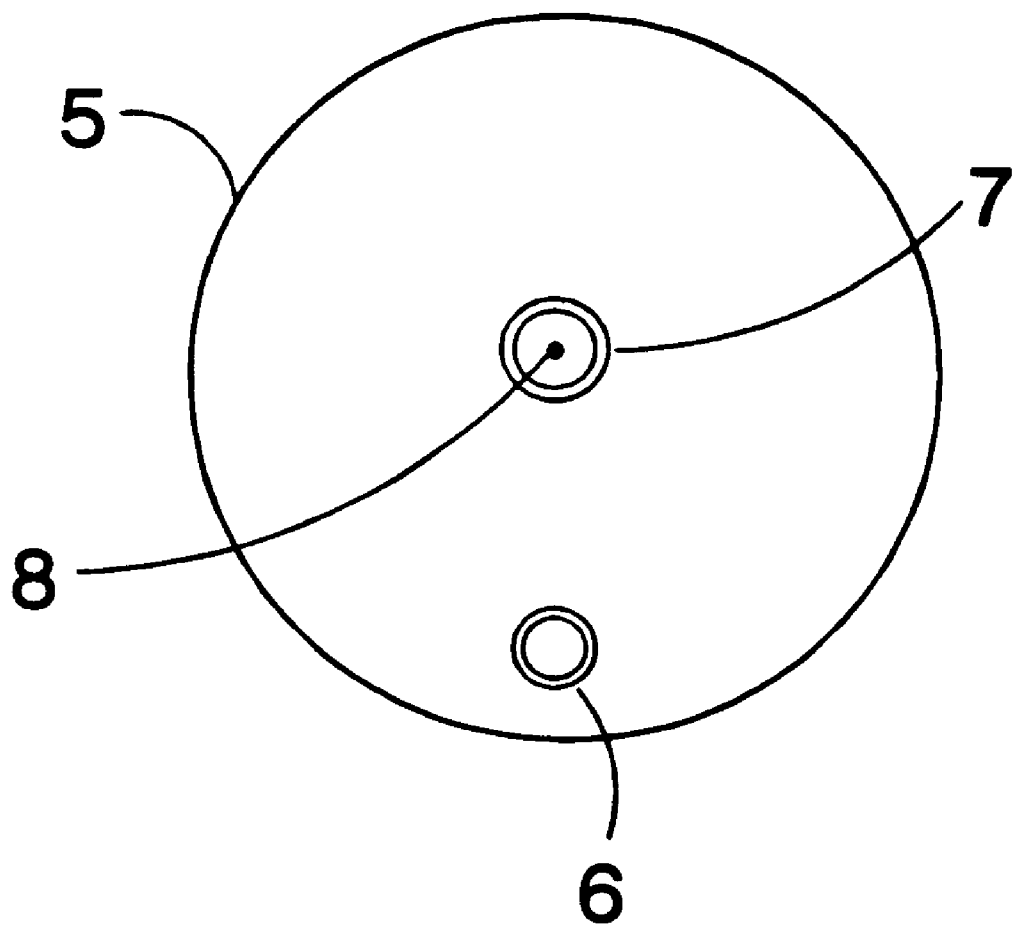
FIG. 3 shows a cross-section of the balloon catheter according to the first embodiment of the present invention.

Referring now to FIG. 3, wherein the same reference numerals of FIG. 2 are applied to the same parts and therefore do not require detailed description, it is seen that the guidewire lumen 6 may be off center with regard to the balloon catheter 5, while the blind lumen 7, which is adapted to encircle the radiation dose delivery wire 8, may be substantially in the center of the balloon catheter 5.

Figure 4:
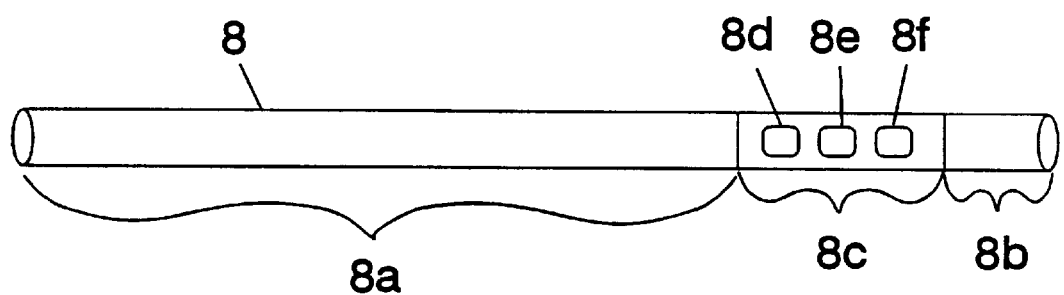
FIG. 4 shows the construction of a radiation dose delivery wire of the present invention.

Referring now to FIG. 4, wherein the same reference numerals of FIG. 2 are applied to the same parts and therefore do not require detailed description, it is seen that the radiation dose delivery wire 8 may include non-radioactive sections 8a and 8b and radioactive section 8c, which has encapsulated or contained within the distal end of radiation dose delivery wire 8, a linear array of radioactive sources 8d, 8e, and 8f, such as pellets of $Ir^{192}$, $I^{125}$, $Pd^{103}$, or other isotopes selected from Table 4, for example. The length of the linear array of pellets may be less than or equal to about 2 cm for use in the coronary artery and less than or equal to about 10 cm for use in periphery arteries. Alternatively, the radioactive source may be composed of a non-linear array of such radioactive pellets or it may be composed of a single radioactive pellet. The radioactivity of each of the radioactive sources 8d, 8e, and 8f may be less than or equal to 10 Curies per centimeter of source.

Figure 15:
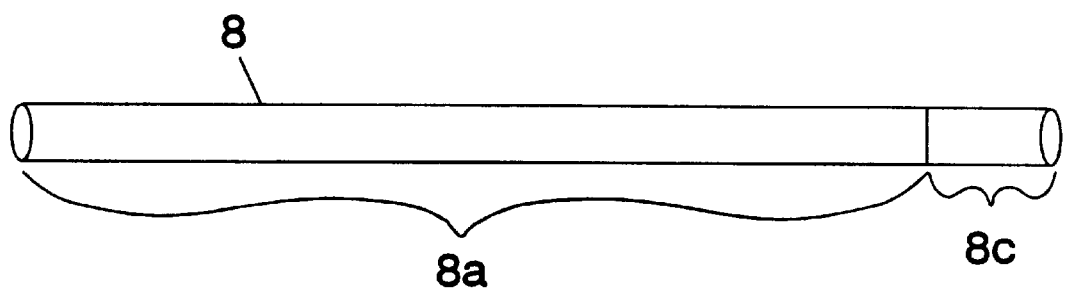
FIG. 15 shows the construction of a radiation dose delivery wire in another embodiment of the present invention.

Referring now to FIG. 15, wherein the same reference numerals of FIG. 4 are applied to the same parts and therefore do not require detailed description, it is seen that the radiation dose delivery wire 8 may include non-radioactive section 8a and radioactive section 8c, which may be attached to or on the distal end of radiation dose delivery wire 8.

Figure 16:
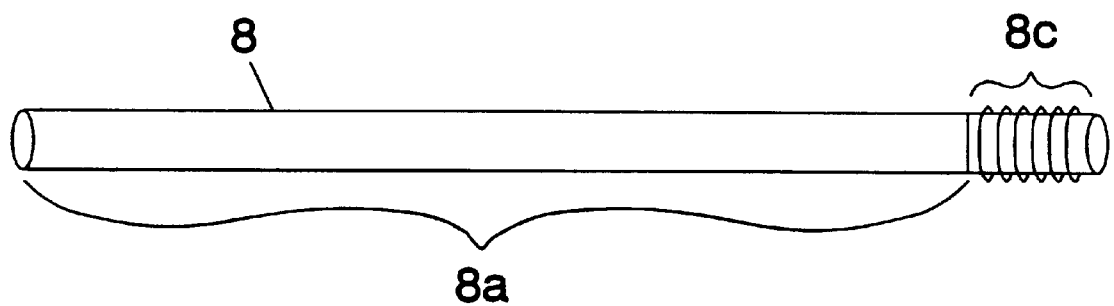
FIG. 16 shows the construction of a radiation dose delivery wire in yet another embodiment of the present invention.

Referring now to FIG. 16, wherein the same reference numerals of FIG. 4 are applied to the same parts and therefore do not require detailed description, it is seen that the radiation dose delivery wire 8 may include non-radioactive section 8a and radioactive section 8c, which may be in the form of a wire wrapped around on the distal end of radiation dose delivery wire 8.

The operation of an apparatus to reduce restenosis after arterial intervention according to the first embodiment of the present invention is as follows, as seen in FIG. 2, for example. The guidewire 9 is inserted into the patient's artery. The distal end of the guidewire 9 is inserted at least as far as, and preferably past the target site, that is, the site that is to receive the dose of radiation. The guidewire 9 is then inserted into the guidewire lumen 6 and the balloon catheter 5 is moved down the guidewire towards the distal end until the balloon section 5a is adjacent the target site. In the case of a balloon angioplasty procedure the balloon section 5a is then inflated and deflated by balloon inflation/deflation inflation means (not shown) connected to the balloon inflation port 13. Alternatively, if it is desired to deliver a dose of radiation to the target area without inflating and deflating the balloon section 5a, such as following an atherectomy or other arterial intervention, the balloon section 1a need not be inflated and deflated.

Finally, the radiation dose delivery wire 8 is inserted into the proximal end of the blind lumen 7 within the balloon catheter 5 through the radiation dose delivery wire entry port 11. The radiation dose delivery wire 8 is inserted towards the distal end of the balloon catheter 5 until the radioactive sources 8d, 8e, and 8f are substantially adjacent the target area. The radioactive sources 8d, 8e, and 8f are left in place until a desired dosage of radiation has been delivered to the target area and then the radiation dose delivery wire 8 is removed from the balloon catheter 5. The length of time that the radioactive sources 8d, 8e, and 8f are left adjacent the target area depends upon the activity of the radioactive sources 8d, 8e, and 8e, the diameter of the artery at the target area, and the desired dosage to be delivered. It should be noted that the radiation dose delivery wire 8 may be oscillated back and forth within the blind lumen 7 so that the radioactive sources 8d, 8e, and 8f may be shorter than the target area while still being able to deliver radiation to the entire target area. In addition, if the radiation dose delivery wire 8 is oscillated back and forth, the time that the radioactive sources 8d, 8e, and 8f must be left adjacent the target area in order to deliver a desired dosage of radiation will also depend upon the length of the target area.

Alternatively, the guidewire 9 may be inserted into the artery as above and a conventional balloon catheter without a blind lumen placed over the guidewire 9 and advanced to the target area to be inflated, deflated, and removed from the artery. After removal from the artery, the balloon catheter 5 of the instant invention, with the blind lumen 7 may be placed over the guidewire 9 utilizing the guidewire lumen 6 and inserted adjacent the target area in order to allow the radiation dose delivery wire 8 to be inserted into the blind lumen 7 to deliver a dosage of radiation to the target area as described above. This procedure permits the use of a conventional balloon catheter to perform an angioplasty procedure before the balloon catheter 5 of the instant invention is utilized to deliver a dose of radiation.

The inventive device and method may also be applied to other luminal structures in a similar manner.

Figure 5:
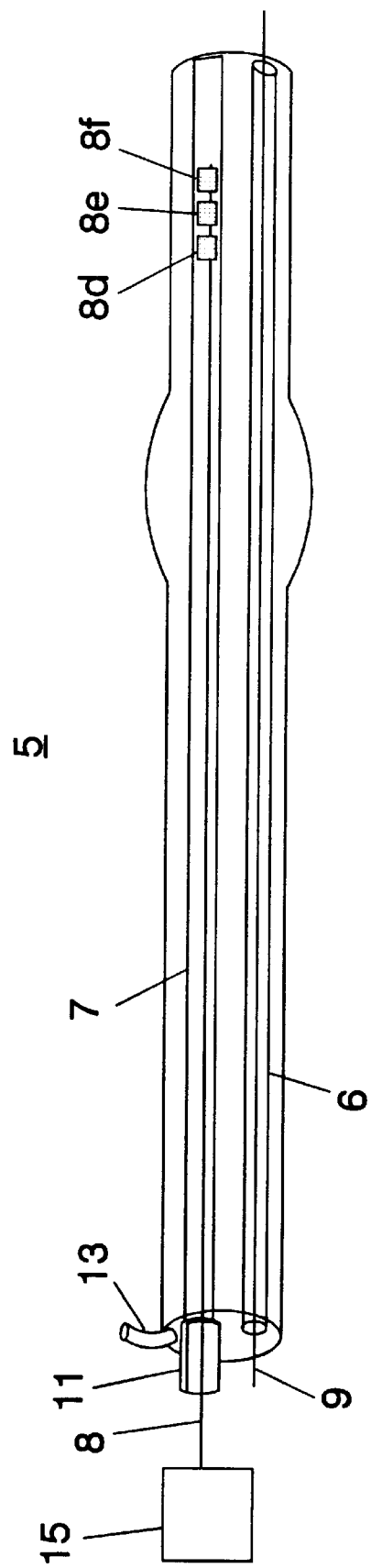
FIG. 5 shows the construction of a second embodiment of the present invention.

Referring now to FIG. 5, wherein the same reference numerals of FIG. 2 are applied to the same parts and therefore do not require detailed description, a balloon catheter according to a second embodiment of the present invention is shown, which can be used to perform the method according to the present invention. In this Fig., a computer controlled afterloader 15, similar to a conventional afterloader such as the one distributed by Nucletron Corp., of Columbia, Md., is connected to the proximal end of the radiation dose delivery wire 8 and is utilized to insert the radiation dose delivery wire 8 into the blind lumen 7 until the radioactive sources 8d, 8e, and 8f are adjacent the target area and to remove the radiation dose delivery wire 8 from the blind lumen 7 after a predetermined dosage of radiation has been delivered to the target area.

The computer controlled afterloader 15 of the present invention differs from the conventional afterloader in that the computer controlled afterloader 15 of the present invention allows an operator to input variables representing the activity of the radioactive sources 8*d*, 8*e*, and 8*f*, the date that the radioactive sources 8*d*, 8*e*, and 8*f* are being delivered adjacent the target area (to take into account decay of the radioactive sources 8*d*, 8*e*, and 8*f*), the diameter of the artery at the target area, the length of the target area, and the value of the desired radioactive dose to be delivered to the target area. The computer controlled afterloader 15 then calculates the time that the radioactive sources 8*d*, 8*e*, and 8*f* must be adjacent the target area to deliver the desired radioactive dosage and then moves the radiation dose delivery wire 8 towards the distal end of the balloon catheter 5 until the radioactive sources 8*d*, 8*e*, and 8*f* are adjacent the target area, waits the calculated time, and then pulls the radiation dose wire 8 back out of the balloon catheter 5.

In addition, the computer controlled afterloader 15 may oscillate the radiation dose delivery wire 8 back and forth while the radioactive sources 8*d*, 8*e*, and 8*f* are adjacent the target area. In this case the computer controlled afterloader 15 would take into account the length of the target area and the rate of oscillation in determining the time necessary to deliver the desired dosage.

The computer controlled afterloader 15 may include a program memory for storing a program to calculate the length of time that the radioactive sources 8*d*, 8*e*, and 8*f* must be adjacent the target area to deliver a desired dosage of radiation, a power supply backup, and a database memory for storing the number of times that a particular radioactive source has been used.

Figure 6:
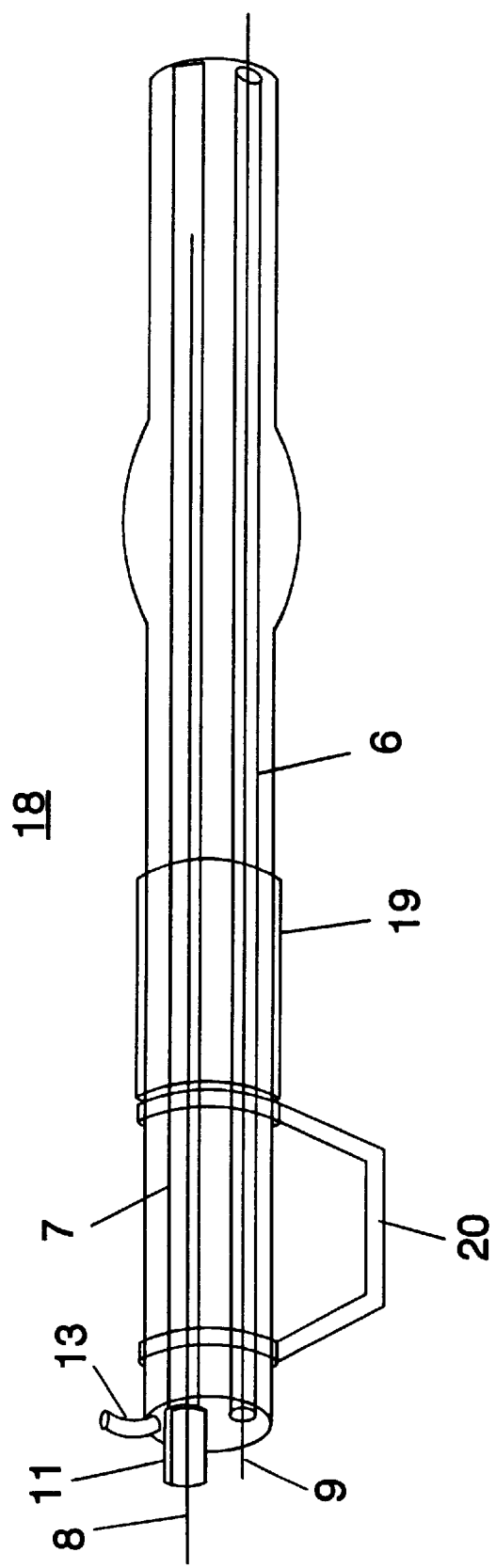
FIG. 6 shows the construction of a third embodiment of the present invention.

Referring now to FIG. 6, wherein the same reference numerals of FIG. 2 are applied to the same parts and therefore do not require detailed description, a balloon catheter 18 according to a third embodiment of the present invention is shown, which can be used to perform the method according to the present invention. A clamp 20 may be utilized to maintain an extended coaxial position between the radiation dose delivery wire entry port 11 connected to the proximal end of the blind lumen 7 and a proximal end of a sheath 19, which surrounds catheter 18 at the area of the incision in the patient's body, during insertion of the radiation dose delivery wire 8 into the blind lumen 7.

Figure 7:
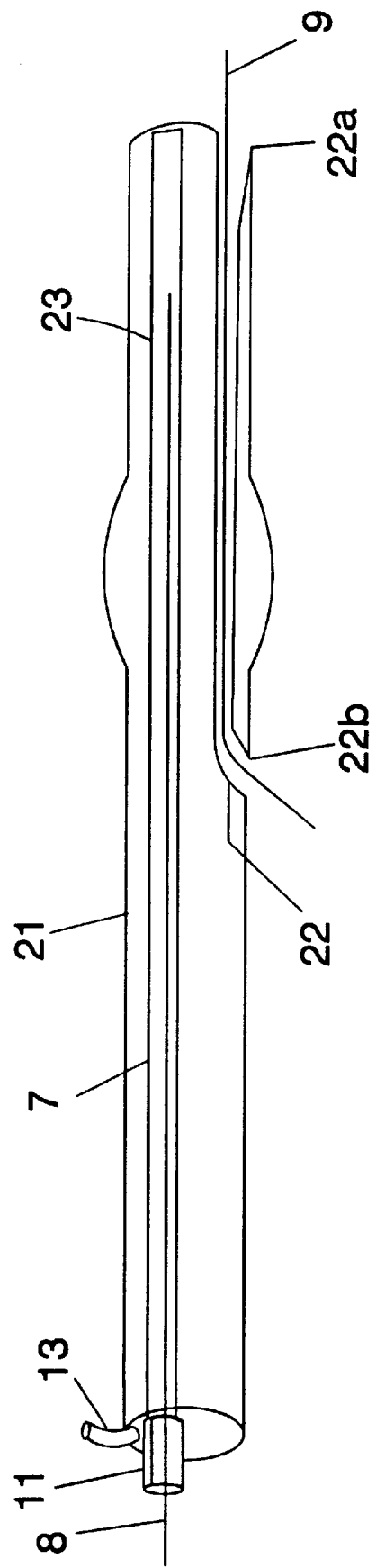
FIG. 7 shows the construction of a fourth embodiment of the present invention.

Referring now to FIG. 7, wherein the same reference numerals of FIG. 2 are applied to the same parts and therefore do not require detailed description, a balloon catheter 21 according to a fourth embodiment of the present invention is shown, which can be used to perform the method according to the present invention. In this Fig., a guidewire lumen 22 extends for a distance less than the length of the balloon catheter 21. That is, the guidewire lumen 22 has an entry point 22*a* at the distal end of balloon catheter 21 and exit point 22*b* along the length of balloon catheter 21, rather than at its proximal end.

As in the first embodiment, the guidewire 9 is inserted into the artery and the guidewire lumen 22 guides the balloon catheter 21 towards the distal end of the guidewire 9. Also, as in the first embodiment, the radiation dose delivery wire 8 rides within the blind lumen 23 of the balloon catheter 21.

Figure 8:
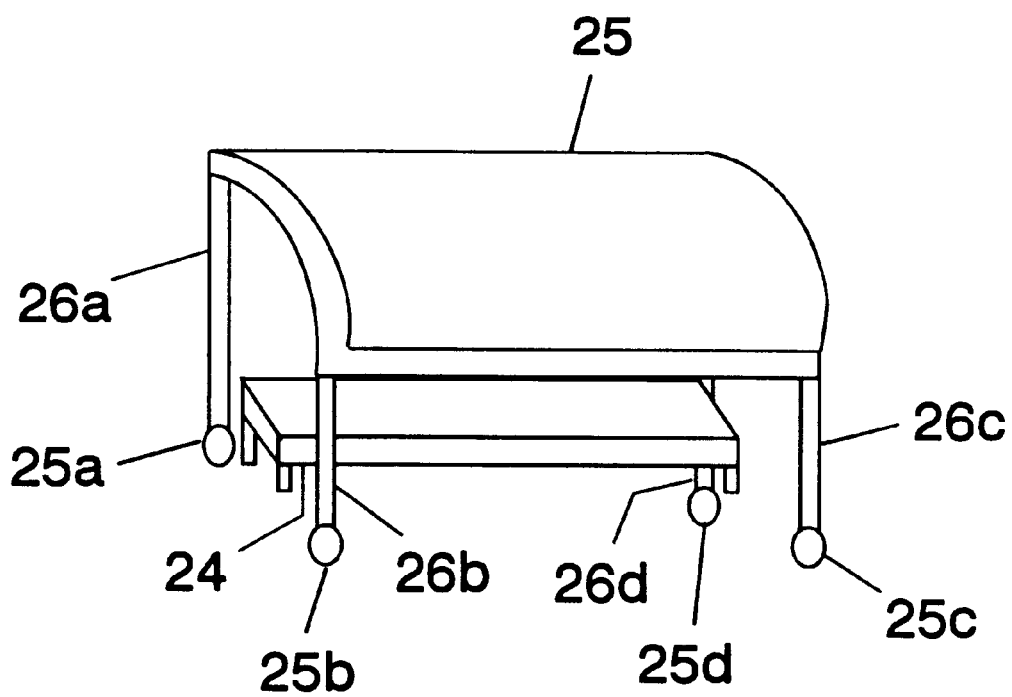
FIG. 8 shows the construction of a fifth embodiment of the present invention.

Referring now to FIG. 8, wherein the same reference numerals of FIG. 2 are applied to the same parts and therefore do not require detailed description, an apparatus according to a fifth embodiment of the present invention is shown, which can be used to perform the method according to the present invention. In this Fig., a radiation shield 25 is movable and is adapted to be moved between a patient (not shown) on a support 24 and an operator of the apparatus (not shown). The radiation shield 25 may, for example, be moveable by means of rollers 25*a*, 25*b*, 25*c*, and 25*d* mounted to legs 26*a*, 26*b*, 26*c*, and 26*d*.

In operation the balloon catheter 5, not shown in this FIG. 8, is inserted into a patient (not shown) who is supported by the support 24 and the radiation shield 25 is moved between an operator of the apparatus and the radiation source 8*d*, 8*e*, and 8*f* within the blind lumen 7 of the balloon catheter 5. The radiation shield 25 is thus adaptable for different sized patients because it is movable and it therefore provides protection to the doctor and other staff from over-exposure to radiation.

Figure 9:
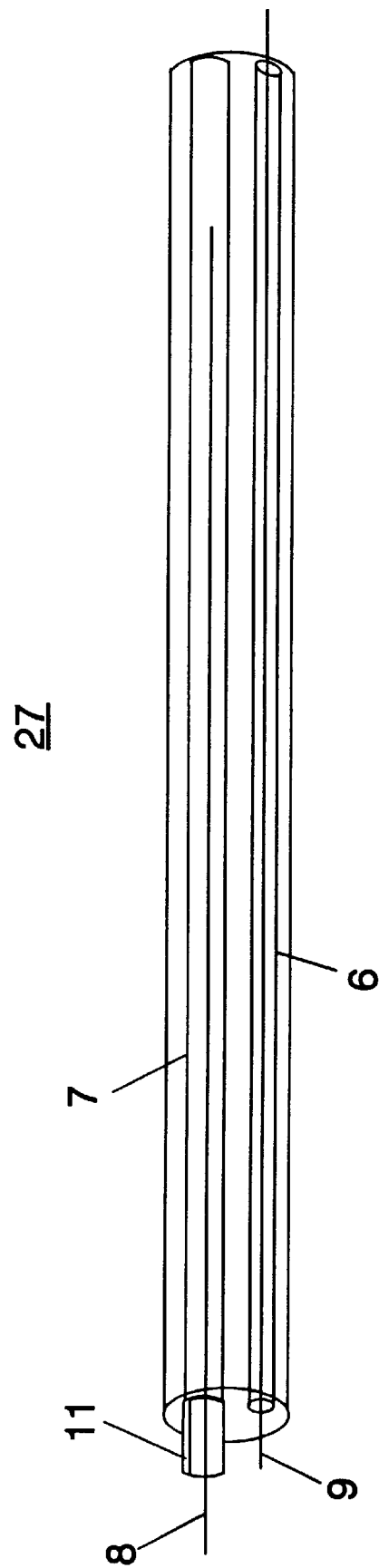
FIG. 9 shows the construction of a sixth embodiment of the present invention.

Referring now to FIG. 9, wherein the same reference numerals of FIG. 2 are applied to the same parts and therefore do not require detailed description, an apparatus according to a sixth embodiment of the present invention is shown, which can be used to perform the method according to the present invention. In this Fig., a catheter without a balloon 27 includes blind lumen 7 and guidewire lumen 6. This embodiment is utilized in a fashion similar to the first embodiment, except here, the apparatus is used only to deliver radiation, and does not have the balloon function of the first embodiment.

Figure 10:
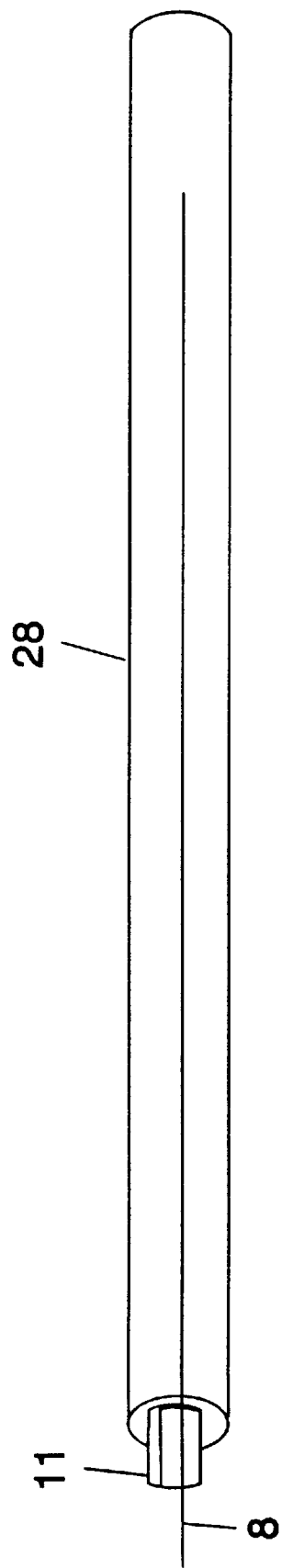
FIG. 10 shows the construction of a seventh embodiment of the present invention.

Referring now to FIG. 10, wherein the same reference numerals of FIG. 2 are applied to the same parts and therefore do not require detailed description, an apparatus according to a seventh embodiment of the present invention is shown, which can be used to perform the method according to the present invention. In this Fig., a blind lumen 28, which accepts radiation dose delivery wire 8 into its proximal end through radiation dose delivery wire entry port 11, is adapted to be removably inserted into a catheter (not shown). The catheter may be a balloon type catheter or it may be a catheter without a balloon.

In operation, the catheter is inserted into a patient in the conventional manner. Blind lumen 28 is then inserted into the catheter and, as in the first embodiment, the radiation dose delivery wire 8 is advanced into the blind lumen 28, through the radiation dose deliver wire entry port 11, until the distal end of the radiation dose delivery wire 8 is adjacent the segment of artery that is to receive a radioactive dose. Also, as in the first embodiment, the radiation dose delivery wire 8 is withdrawn after a desired dose of radiation has been delivered to the artery segment. This embodiment is intended primarily, but not exclusively, for procedures in the peripheral vascular areas.

Figure 17:
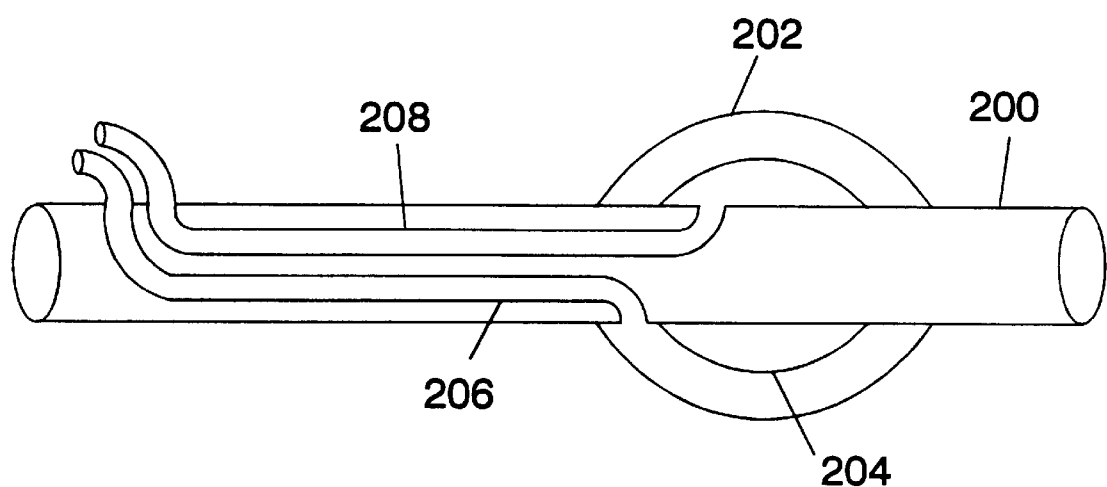
FIG. 17 shows a dual-balloon catheter according to an embodiment of the present invention.

Referring now to FIG. 17, this Fig. shows a dual-balloon catheter according to an embodiment of the present invention. Guidewire lumen 200 may be provided for insertion into a patient (not shown) over a guidewire (not shown). Guidewire lumen 200 may pass through outer balloon 202 as well as inner balloon 204. Inner balloon 204 may be substantially concentric with outer balloon 202. Outer balloon 200 may be inflated through outer balloon lumen 206 and inner balloon 204 may be inflated through inner balloon lumen 208. The inner and outer balloons are preferably independently inflatable and the inner balloon lumen and outer balloon lumen may pass inside the guidewire lumen, as shown, or may pass outside the guidewire lumen. It must be noted that a guidewire lumen does not have to be used with the inventive dual-balloon catheter.

The inner and outer balloons may both be inflated with a radioactive fluid or either one of them may be so inflated. For the purposes of this application the term fluid refers to an aqueous solution as well as a gas phase. If only the inner balloon is inflated with a radioactive fluid the outer balloon provides extra protection to the patient in the case of rupture of the inner balloon (the outer balloon will help to contain the fluid). If only the outer balloon is inflated with the radioactive fluid then a reduced amount of radioactive fluid is required to achieve a given radiation therapy.

In this regard it is noted that the present invention provides for the reduction in volume of radioactive fluid, minimizes the risk of rupture, adds shielding, removes the operator from the vicinity of the radioactive fluid, and reduces the reduces the risk of a spill of the radioactive fluid.

Figure 18:
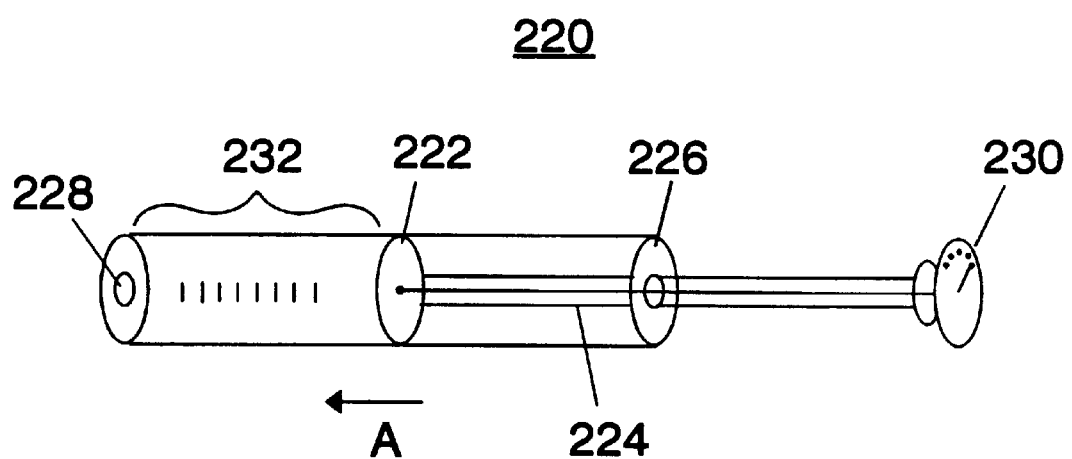
FIG. 18 shows an indiflator according to an embodiment of the present invention.

Referring now to FIG. 18, a novel indiflator 220 is shown. In this indiflator a plunger head 222 is attached to a plunger stem 224. The plunger stem is threaded and may be locked by lock 226. The plunger stem may be moved in the direction of arrow A in order to force fluid out through port 228, which may be connected to a Luer lock (not shown) and ultimately to a balloon catheter (not shown). A pressure indicator 230 measures the pressure of the fluid acted upon by the plunger through a transducer means connected thereto by a connector running in or along the stem 224. This arrangement allows for the measurement of pressure as described above while minimizing the volume of fluid acted upon by the plunger. Calibration scale 232 may be provided for measuring fluid volume and this calibration scale 232 may read from 1 to 5 cc's in 0.1 cc increments, for example.

Referring now to FIG. 19, a shield 240 is shown. This shield may slid over the indiflator 220 of FIG. 18 and may be provided with a Lucite section 242 and a lead section 244 for protecting an operator from the radioactive fluid. The lead section may have a window therein (not shown) to allow an operator to seen the indiflator 220. The Lucite section 242 may be aligned with the calibration scale 232 of the indiflator 220, for example.

Figure 20:
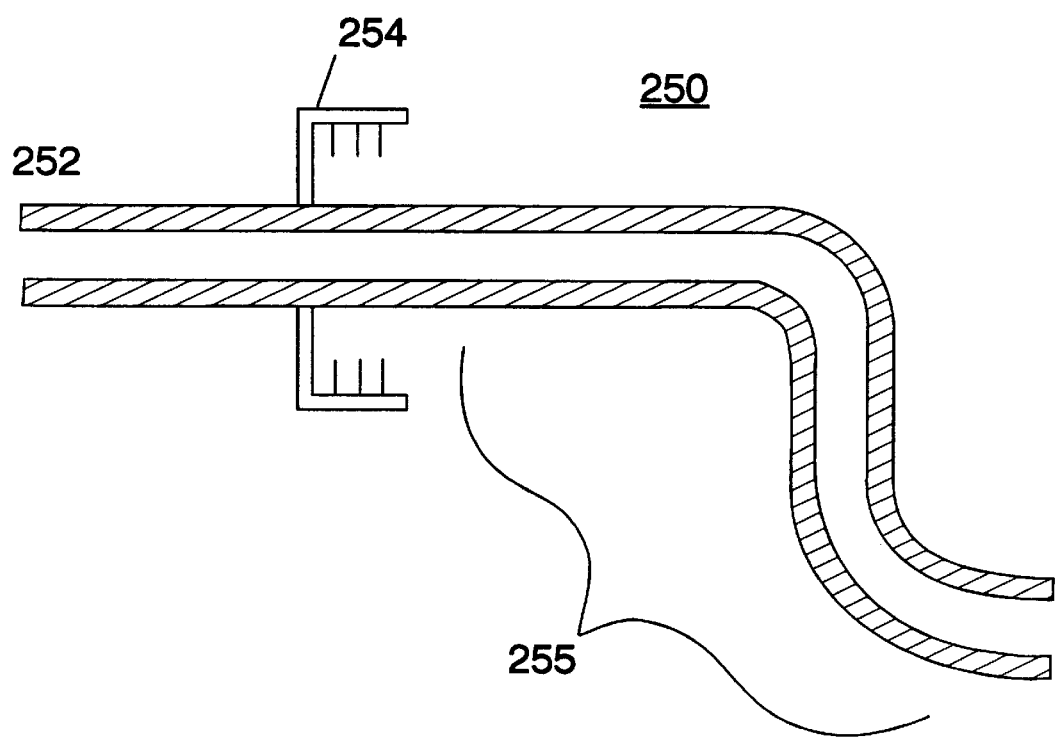
FIG. 20 shows a lumen according to an embodiment of the present invention.

Referring now to FIG. 20, this Fig. shows a lumen 250 that may be placed between an indiflator (not shown) or a Luer lock (not shown) and a balloon catheter (not shown). End 252 of the lumen 250 may be attached to the indiflator or Luer lock, threaded attachment ring 254 may be attached to the balloon catheter and section 255 may be placed 'within the lumen of the balloon catheter to take up space and decrease the volume of radioactive fluid inserted into the balloon catheter when it is inflated with a fluid, such as a radioactive fluid.

Figure 21:
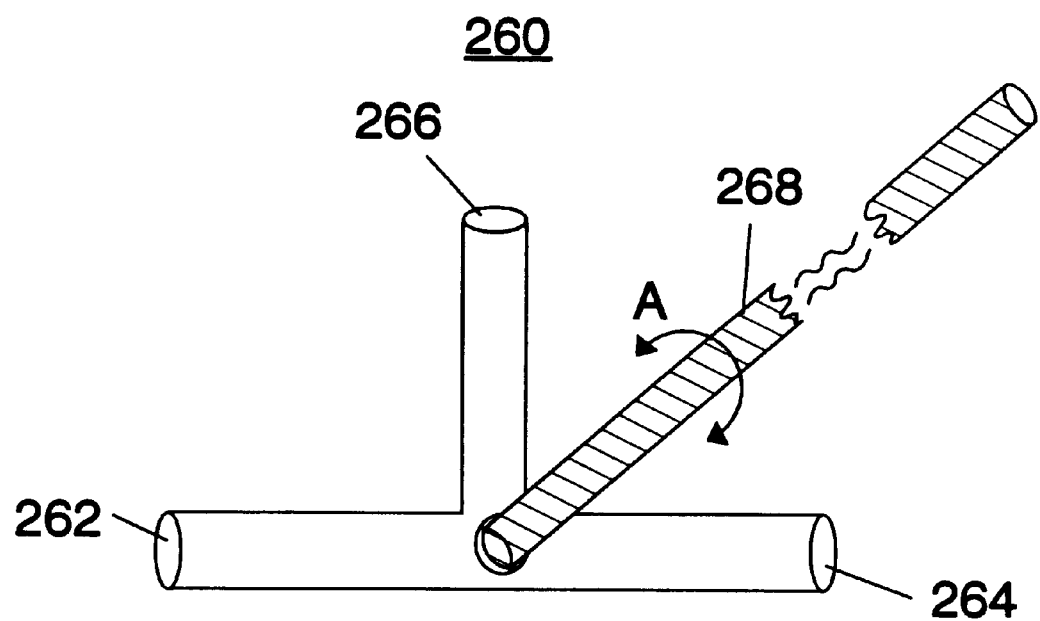
FIG. 21 shows a 3-way stopcock according to an embodiment of the present invention.

Referring now to FIG. 21, a 3-way stopcock 260 is shown for connection between a indiflator (not shown) or a Luer lock (not shown) and a balloon catheter (not shown). Port 262 may be connected to the indiflator or the Luer lock and port 264 may be connected to the balloon catheter. Port 266 may be used to vent the balloon catheter to the outside atmosphere or to a syringe (not shown) or storage container (not shown). Handle 268, which controls a valve (not shown) within the 3-way stopcock is moveable along arrow A to allow passage of fluid between two of the ports. The handle 268 is long in relation to the 3-way stopcock so that an operator's hands are not near the radioactive fluid.

Figure 22:
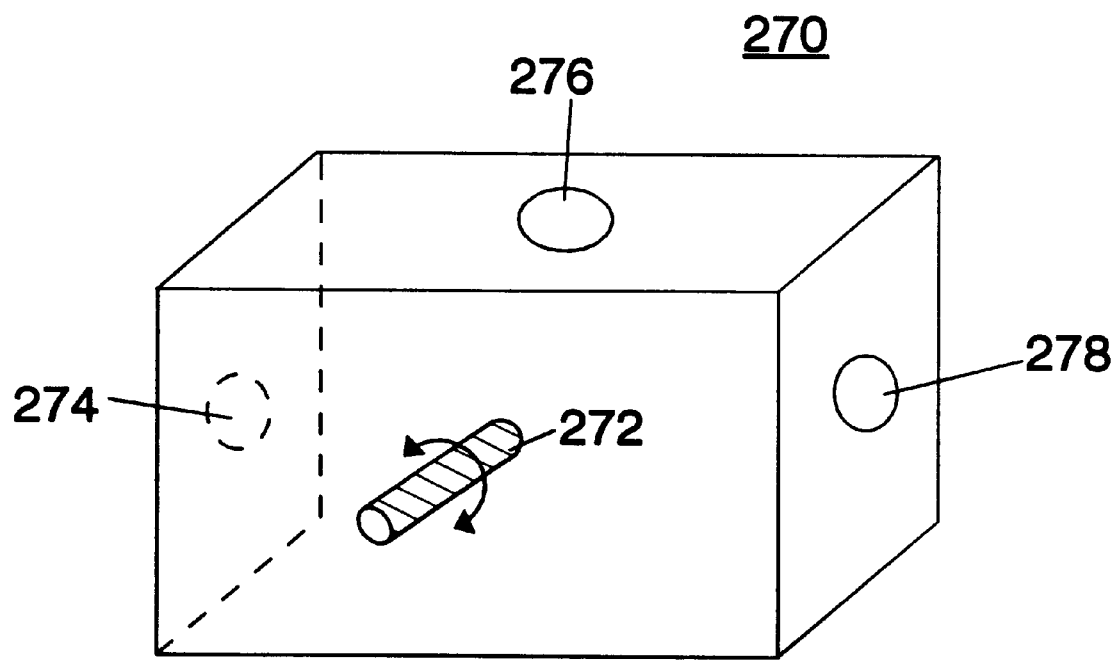
FIG. 22 shows a case for a 3-way stopcock according to an embodiment of the present invention.

Referring now to FIG. 22, a case 270 for a 3-way stopcock is shown. The case may include a 'handle 272 for actuating the 3-way stopcock. The case may also include apertures 274, 276, and 278 for permitting fluid flow to and from the 3-way stopcock. The case 270 may be designed to accept a separate 3-way stopcock or may include a 3-way stopcock integrally therewith. The case 270 may be made of, or include a layer of either or both Lucite and lead, for example (to reduce an operator's exposure to radiation).

Figure 23:
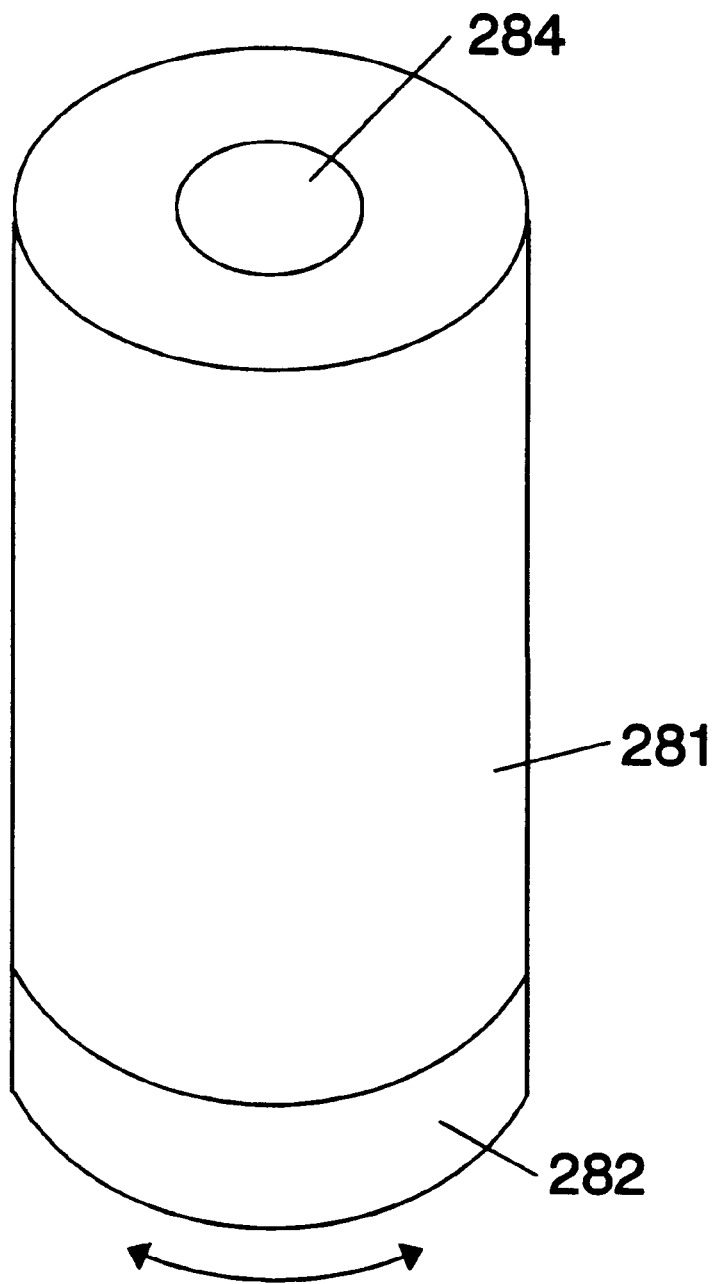
FIG. 23 shows a container for holding a radioactive substance according to an embodiment of the present invention.

Referring now to FIG. 23, a container 280 for holding a radioactive substance, such as a fluid is shown. A bottom 282 may unscrew from the top 281 in order to place a bottle with a radioactive fluid inside. A hole 284 in the top may be provided for providing access to the radioactive fluid inside the container. The hole 284 may be covered with a sealing structure, such as a rubber membrane, for example, as may be the bottle. This sealing structure may be self-sealing. If a sealing stricture is used, a needle may be employed to pierce the sealing structure and access the radioactive fluid. The exterior of the container 280 may be lead and the interior may be Lucite, for example. Alternatively, the interior may be lead and the exterior Lucite. This two-layer structure provides protection from the radioactive substance contained therein.

Figure 24:
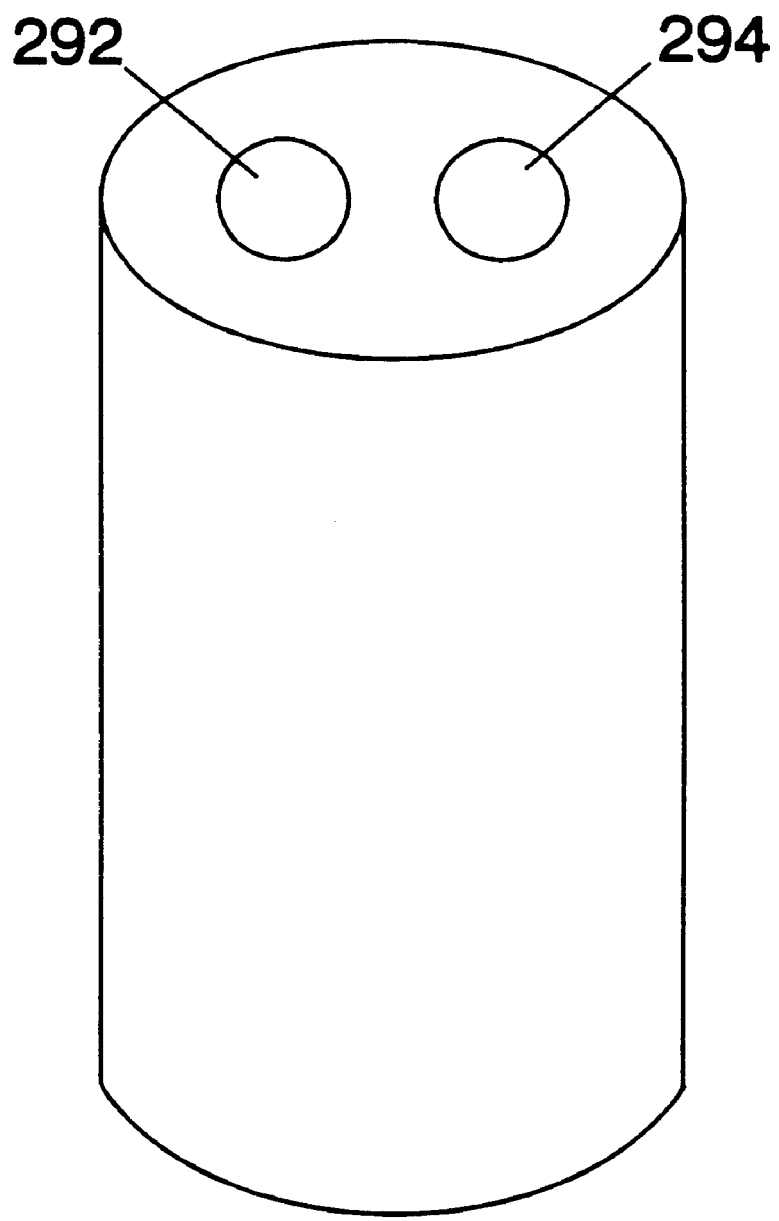
FIG. 24 shows another container for holding a radioactive substance according to an embodiment of the present invention.

Referring now to FIG. 24, another container 290 for holding a radioactive substance, such as a fluid is shown. A first port 292 may be provided for inserting a radioactive fluid and a second port 294 may be provided for removing the radioactive fluid. Like the container 280 of FIG. 23, the ports may be covered with a sealing structure, such as a rubber membrane, for example. This sealing structure may be self-sealing. If a sealing stricture is used, a needle may be employed to pierce the sealing structure and access the radioactive fluid. The exterior of the container 290 may be lead and the interior may be Lucite, for example. Alternatively, the interior may be lead and the exterior Lucite. This two-layer structure provides protection from the radioactive substance contained therein.

Figure 25:
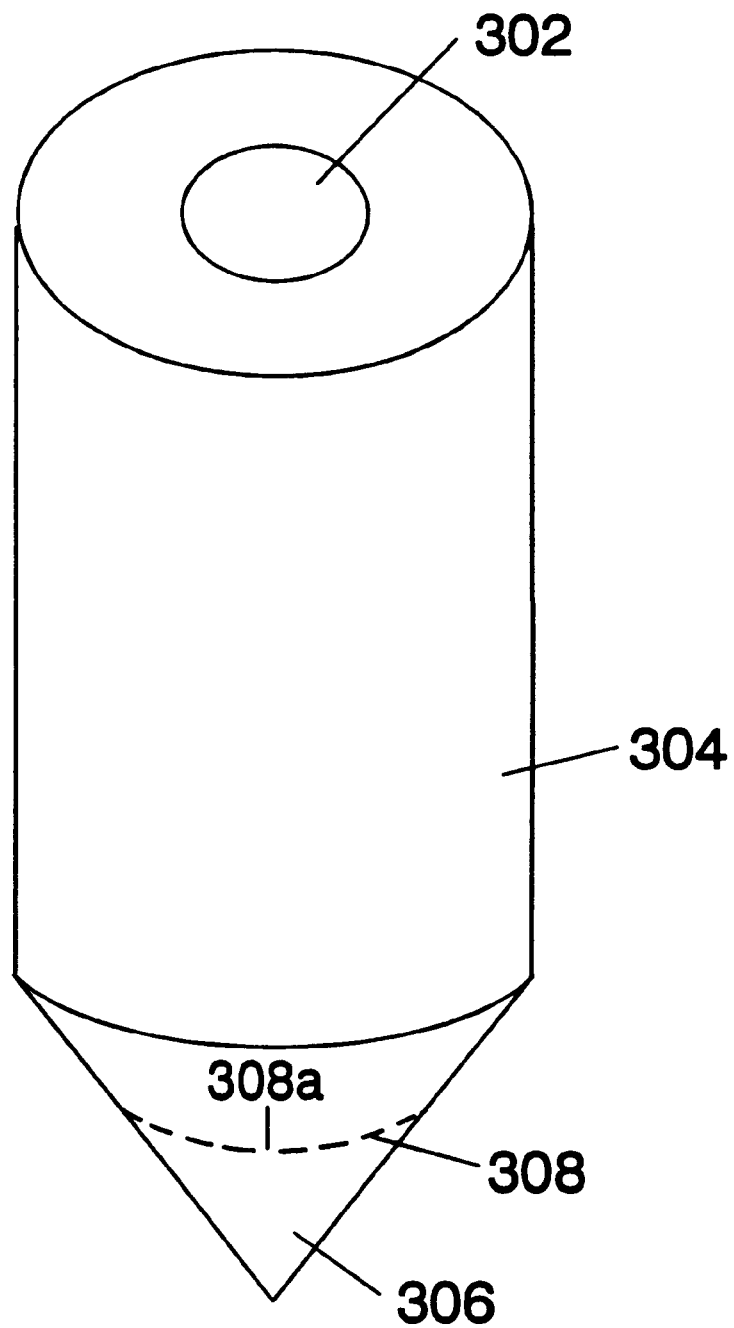
FIG. 25 shows another container for holding a radioactive substance according to an embodiment of the present invention.

Referring now to FIG. 25, another container 300 for holding a radioactive substance, such as a fluid is shown. A port 302 may be provided for inserting and removing a radioactive fluid. Like the container 280 of FIG. 23, the port may be covered with a sealing structure, such as a rubber membrane, for example. This sealing structure may be self-sealing. If a sealing stricture is used, a needle may be employed to pierce the sealing structure and access the radioactive fluid. The exterior of the container 300 may be lead and the interior may be Lucite, for example. Alternatively, the interior may be lead and the exterior Lucite. This two-layer structure provides protection from the radioactive substance contained therein. The top section 304 may be generally cylindrical and the bottom section 306 may be conical, or funnel-shaped. The funnel-shaped bottom section 306 concentrates the fluid at the bottom of the container 300 in a small volume so that it may be removed by a needle placed down into the bottom section. A mesh 308 with a central hole 308a may be employed to strain the fluid and keep relatively large debris above the mesh.

Figure 26:
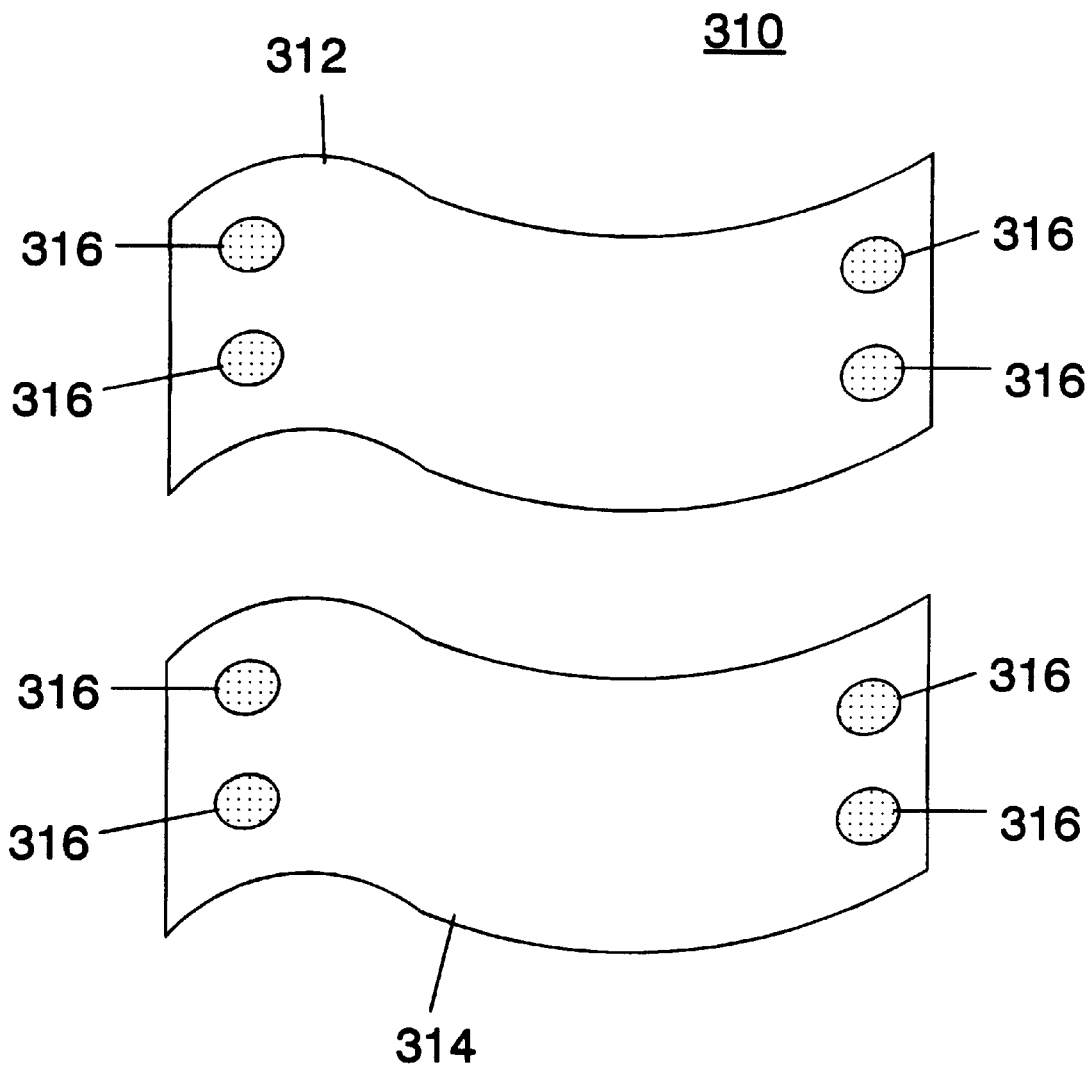
FIG. 26 shows a flexible plastic shield according to an embodiment of the present invention.

Referring now to FIG. 26, a flexible plastic shield 310 is shown. This shield 310 may include sections 312 and 314 and may include fasteners 316 such as snaps or Velcro for holding the shield around a container or structure with a radioactive source whereby the shield protects a person from the radiation given off by the radioactive source. A flexible plastic shield having a density approximately equal to that of water should be approximately 2 mm thick to contain beta energy, for example.

It must be noted that although the present invention is described by reference to particular embodiments thereof, many changes and modifications of the invention may become apparent to those skilled in the art without departing from the spirit and scope of the invention as set forth in the claims. For example, isotopes chosen from the attached Tables may be substituted for those identified elsewhere in the application.

TABLE 1

Basic Properties of Isotopes

| isotope | decay | emission | maximum energy | average energy | t½ | gamma factor[1] | activity[2] |
|---|---|---|---|---|---|---|---|
| Ir-192 | beta- | gamma | 612 keV | 375 keV | 74 d | 4.6 | 1000 mCi |
| I-125 | EC | x-ray | 35 keV | 28 keV | 60 d | 1.2 | 3700 mCi |
| Pd-103 | EC | x-ray | 21 keV | 21 keV | 17 d | 1.1 | 3700 mCi |
| P-32 | beta- | beta- | 1.71 MeV | 690 keV | 14 d | — | 36 mCi |
| Sr-90 | beta- | beta- | 2.27 MeV | 970 keV[3] | 28 yr | — | 30 mCi |

[1]R-cm2/hr-mCi
[2]For dose rate of 5Gy/min at 2 mm distance, source diameter = 0.65 mm, length = 2.0 cm
[3]In equilibrium with Y-90

TABLE 2

| A | ELEMENT | Decay Mode | Half-Life | Rad. Type | | average Radiation Energy (keV) | | Radiation Intensity (%) | |
|---|---|---|---|---|---|---|---|---|---|
| 26 | AL 0.947 | EC | 7.4E + 5 Y 3 | B+ | | 543.49 | 7 | 81.77 | 17 |
| 123 | SN 1.11 | B– | 129.2 D 4 | B– | TOT | 522.7 | 14 | 100.00 | 13 |
| 123 | SN 1.11 | B– | 129.2 D 4 | B– | | 525.5 | 13 | 99.37 | 11 |
| 40 | K 1.07 | B– | 1.277E + 9 Y | B– | | 560.64 | 18 | 89.27 | 13 |
| 89 | SR 1.24 | B– | 50.53 D 7 | B– | | 583.3 | 13 | 99.99039 | 8 |
| 91 | Y 1.29 | B– | 58.51 D 6 | B– | TOT | 603.4 | 9 | 100.00 | 7 |
| 91 | Y 1.28 | B– | 58.51 D 6 | B– | | 604.9 | 9 | 99.70 | 5 |
| 115 | CD 1.29 | B– | 44.6 D 3 | B– | TOT | 605.2 | 10 | 99.98 | |
| 115 | CD 1.07 | B– | 44.6 D 3 | B– | | 618.3 | 9 | 97.00 | |
| 89 | SR 1.24 | B– | 50.53 D 7 | B– | | 583.3 | 13 | 99.99039 | 8 |
| 91 | Y 1.29 | B– | 58.51 D 6 | B– | TOT | 603.4 | 9 | 100.00 | 7 |
| 91 | Y 1.28 | B– | 58.51 D 6 | B– | | 604.9 | 9 | 99.70 | 5 |
| 115 | CD 1.29 | B– | 44.6 D 3 | B– | TOT | 605.2 | 10 | 99.98 | |
| 115 | CD 1.28 | B– | 44.6 D 3 | B– | | 618.3 | 9 | 97.00 | |
| 86 | RB 1.42 | B– | 18.631 D 1 | B– | TOT | 668.1 | 10 | 100.00 | 6 |
| 32 | P 1.48 | B– | 14.26 D 4 | B– | | 694.9 | 3 | 100.0 | |
| 86 | RB 1.38 | B– | 18.631 D 1 | B– | | 709.3 | 9 | 91.36 | 4 |

TABLE 3

| A | ELEMENT | Decay Mode | Half-Life | Rad. Type | Radiation Energy (keV) | | Radiation Intensity (%) | |
|---|---------|------------|-----------|-----------|------------------------|---|-------------------------|---|
| 43 | SC 0.767 | EC | 3.891 H 12 | B+ | 508.1 | 9 | 70.9 | 6 |
| 61 | CU 0.569 | EC | 3.333 H 5 | B+ | 524.2 | 5 | 51. | 5 |
| 73 | SE 0.778 | EC | 7.15 M 8 | B− | 562. | 5 | 65.0 | 7 |
| 73 | SE 0.789 | EC | 7.15 H 8 | B+ | TOT | 564. | 5 | 65.7 | 7 |
| 55 | CO 0.917 | EC | 17.53 H 3 | B+ | TOT | 567.07 | 21 | 76. | 4 |
| 44 | SC 1.27 | EC | 3.927 H 8 | B+ | 632.6 | 9 | 94.34 | 4 |
| 90 | NB 0.721 | EC | 14.60 H 5 | B+ | 662.2 | 18 | 51.1 | 18 |
| 75 | BR 1.09 | EC | 96.7 M 13 | B+ | 710. | 10 | 72. | 6 |
| 75 | BR 0.721 | EC | 96.7 M 13 | B+ | 749. | 10 | 52. | 4 |
| 75 | BR 1.09 | EC | 96.7 M 13 | B+ | TOT | 710. | 10 | 72. | 6 |
| 75 | BR 0.830 | EC | 96.7 M 13 | B+ | 749. | 10 | 52. | 4 |
| 85 | Y 1.35 | EC | 2.68 H 5 | B+ | TOT | 749. | 6 | 84. | 19 |
| 77 | BR 1.30 | EC | 74.4 M 6 | B+ | TOT | 760. | 14 | 80. | 4 |
| 68 | GA 1.58 | EC | 67.629 M 2 | B+ | TOT | 829.9 | 6 | 89.1 | 5 |
| 68 | GA 1.57 | EC | 67.629 M 2 | B+ | 836.0 | 6 | 88.0 | 4 |
| 89 | NB 1.36 | EC | 1.18 H 2 | B+ | 986. | 21 | 65. | 6 |
| 85 | Y 1.22 | EC | 4.86 H 13 | B+ | TOT | 987. | 5 | 58. | 5 |
| 89 | NB 1.36 | EC | 1.18 M 2 | B+ | 986. | 21 | 65. | 6 |
| 85 | Y 1.22 | EC | 4.86 H 13 | B+ | TOT | 987. | 5 | 58. | 5 |
| 89 | NB 1.73 | EC | 1.18 H 2 | B+ | TOT | 1002. | 22 | 81. | 10 |
| 85 | Y 1.12 | EC | 4.86 H 13 | B+ | 1008. | 5 | 52. | 4 |
| 87 | ZR 1.81 | EC | 1.68 H 1 | B− | TOT | 1009. | 5 | 84.0 | 6 |
| 110 | IN 1.33 | EC | 69.1 M 5 | B+ | TOT | 1010. | 14 | 62. | 4 |
| 87 | ZR 1.80 | EC | 1.68 H 1 | B+ | 1012. | 5 | 83.5 | 6 |
| 110 | IM 1.32 | EC | 69.1 M 5 | B+ | 1015. | 14 | 61. | 4 |
| 72 | AS 1.80 | EC | 26.0 H 1 | B+ | 1117.0 | 19 | 64.2 | 15 |
| 110 | IN 1.32 | EC | 69.1 M 5 | B+ | 1015. | 14 | 61. | 4 |
| 72 | AS 1.53 | EC | 26.0 H 1 | B+ | 1117.0 | 19 | 64.2 | 15 |
| 72 | AS 2.18 | EC | 26.0 H 1 | B+ | TOT | 1167.8 | 20 | 87.8 | 23 |
| 76 | BR 1.38 | EC | 16.2 H 2 | B+ | TOT | 1180. | 11 | 55. | 3 |
| 89 | NB 2.32 | EC | 1.9 H 2 | B+ | TOT | 1447. | 10 | 75. | 15 |
| 89 | NB 2.30 | EC | 1.9 H 2 | B+ | 1462. | 9 | 74. | 15 |
| 148 | TB 1.71 | EC | 60 M 1 | B+ | TOT | 1558. | 20 | 51.38 | |
| 120 | I 2.76 | EC | 81.0 M 6 | B+ | TOT | 1657. | 99 | 78.34 | |
| 148 | TB 1.71 | EC | 60 M 1 | B+ | TOT | 1558. | 20 | 51.38 | |
| 120 | I 2.76 | EC | 81.0 M 6 | B+ | TOT | 1657. | 99 | 78.34 | |
| 66 | GA 2.07 | EC | 9.49 H 7 | B+ | TOT | 1736.6 | 20 | 56.1 | 15 |
| 72 | GA | B− | 14.10 H 1 | B− | TOT | 501.6 | 15 | 100.2 | 12 |

TABLE 3-continued

| A | ELEMENT | Decay Mode | Half-Life | Rad. Type | Radiation Energy (keV) | | Radiation Intensity (%) | |
|---|---------|------------|-----------|-----------|------------------------|----|------|----|
| | 1.07 | | | | | | | |
| 127 | SH | B– | 2.10 H 4 | B– TOT | 511. | 74 | 103. | 10 |
| | 1.12 | | | | | | | |
| 129 | TE | B– | 69.6 M 2 | B– TOT | 520.2 | 19 | 99. | 12 |
| | 1.10 | | | | | | | |
| 122 | SB | B– | 2.7238 D 2 | B– | 521.2 | 10 | 66.73 | 20 |
| | 0.741 | | | | | | | |
| 140 | LA | B– | 1.6781 D 7 | B– TOT | 524.5 | 10 | 97.3 | 25 |
| | 1.09 | | | | | | | |
| 71 | ZN | B– | 3.96 H 5 | B– TOT | 540. | 6 | 99. | 3 |
| | 0.741 | | | | | | | |
| 140 | LA | B– | 1.6781 D 7 | B– TOT | 524.5 | 10 | 97.3 | 25 |
| | 1.09 | | | | | | | |
| 71 | ZN | B– | 3.96 H 5 | B– TOT | 540. | 6 | 99. | 3 |
| | 1.14 | | | | | | | |
| 129 | TE | B– | 69.6 M 2 | B– | 544.5 | 18 | 88. | 12 |
| | 1.02 | | | | | | | |
| 24 | NA | B– | 14.9590 H | B– | 554.1 | 3 | 99.944 | 4 |
| | 1.18 | | | | | | | |
| 71 | ZN | B– | 3.96 H 5 | B– | 573. | 5 | 89. | 3 |
| | 1.09 | | | | | | | |
| 122 | SB | B– | 2.7238 D 2 | B– TOT | 574.4 | 11 | 97.4 | 6 |
| | 1.19 | | | | | | | |
| 31 | SI | B– | 157.3 M 3 | B– | 595.6 | 4 | 99.93 | |
| | 1.27 | | | | | | | |
| 190 | RE | B– | 3.2 H 2 | B– TOT | 621. | 95 | 53. | 5 |
| | 0.703 | | | | | | | |
| 31 | SI | B– | 157.3 M 3 | B– | 595.6 | 4 | 99.93 | |
| | 1.27 | | | | | | | |
| 190 | RE | B– | 3.2 H 2 | B– TOT | 621. | 95 | 53. | 5 |
| | 0.703 | | | | | | | |
| 65 | NI | B– | 2.51719 H | B– TOT | 627.7 | 8 | 100.0 | 4 |
| | 1.34 | | | | | | | |
| 77 | GE | B– | 11.30 H 1 | B– TOT | 641.8 | 13 | 100.1 | 21 |
| | 1.37 | | | | | | | |
| 91 | SR | B– | 9.63 H 5 | B– TOT | 646.6 | 23 | 99. | 6 |
| | 1.37 | | | | | | | |
| 166 | HO | B– | 26.80 H 2 | B– TOT | 665.1 | 6 | 100. | 3 |
| | 1.42 | | | | | | | |
| 145 | PR | B– | 5.984 H 10 | B– TOT | 675. | 3 | 97.3 | 21 |
| | 1.40 | | | | | | | |
| 152 | EU | B– | 9.274 H 9 | B– TOT | 676.9 | 9 | 73. | 4 |
| | 1.05 | | | | | | | |
| 145 | PR | B– | 5.984 H 10 | B– | 683. | 3 | 95.0 | 20 |
| | 1.40 | | | | | | | |
| 152 | EU | B– | 9.274 H 9 | B– TOT | 676.9 | 9 | 73. | 4 |
| | 1.05 | | | | | | | |
| 145 | PR | B– | 5.984 H 10 | B– | 683. | 3 | 95.0 | 20 |
| | 1.38 | | | | | | | |
| 166 | HO | B– | 26.80 H 2 | B– | 693.6 | 5 | 50.0 | 21 |
| | 0.739 | | | | | | | |
| 152 | EU | B– | 9.27 H 9 | B– | 705.4 | 8 | 68. | 4 |
| | 1.02 | | | | | | | |
| 97 | ZR | B– | 16.91 H 5 | B– TOT | 706.6 | 10 | 99.4 | 5 |
| | 1.50 | | | | | | | |
| 150 | PM | B– | 2.68 H 2 | B– TOT | 725. | 36 | 100. | 6 |
| | 1.55 | | | | | | | |
| 97 | ZR | B– | 16.91 H 5 | B– | 757.0 | 9 | 87.8 | 3 |
| | 1.42 | | | | | | | |
| 113 | AG | B– | 9.37 H 5 | B– | 757. | 10 | 100.4 | |
| | 1.62 | | | | | | | |
| 97 | ZR | B– | 16.91 H 5 | B– | 757.0 | 9 | 87.8 | 3 |
| | 1.42 | | | | | | | |
| 113 | AG | B– | 5.37 H 5 | B– TOT | 757. | 10 | 100.4 | |
| | 1.62 | | | | | | | |
| 188 | RE | B– | 16.98 H 2 | B– TOT | 763.81 | 19 | 100.0 | 21 |
| | 1.63 | | | | | | | |
| 212 | BI | B– | 60.55 M 6 | B– TOT | 769.6 | 19 | 64.06 | 14 |
| | 1.05 | | | | | | | |
| 113 | AG | B– | 5.37 H 5 | B– | 791. | 10 | 85.00 | |
| | 1.43 | | | | | | | |
| 188 | RE | B– | 16.98 H 2 | B– | 795.30 | 18 | 70.6 | 15 |
| | 1.20 | | | | | | | |
| 194 | IR | B– | 19.15 H 3 | B– TOT | 806.8 | 9 | 100.0 | 25 |
| | 1.72 | | | | | | | |

TABLE 3-continued

| A | ELEMENT | Decay Mode | Half-Life | Rad. Type | | Radiation Energy (keV) | | Radiation Intensity (%) | |
|---|---|---|---|---|---|---|---|---|---|
| 142 | PR 1.72 | B- | 19.12 H 5 | B- | TOT | 809.1 | 12 | 100.0 | 7 |
| 56 | MN 1.72 | B- | 2.5785 H 6 | B- | TOT | 829.9 | 7 | 100.1 | 14 |
| 142 | PR 1.72 | B- | 19.12 H 5 | B- | TOT | 809.1 | 12 | 100.0 | 7 |
| 56 | MN 1.77 | B- | 2.5785 H 6 | B- | TOT | 829.9 | 7 | 100.1 | 14 |
| 212 | BI 0.983 | B- | 60.55 M 6 | B- | | 832.5 | 17 | 55.46 | 10 |
| 142 | PR 1.71 | B- | 19.12 H 5 | B- | | 833.4 | 11 | 96.3 | 5 |
| 194 | IR 1.54 | B- | 19.15 H 3 | B- | | 846.4 | 8 | 85.4 | 20 |
| 142 | LA 1.85 | B- | 91.1 M 5 | B- | TOT | 872. | 4 | 99.4 | 10 |
| 65 | NI 1.12 | B- | 2.51719 M | B- | | 875.4 | 6 | 60.0 | 3 |
| 139 | BA 1.89 | B- | 83.06 M 28 | B- | TOT | 889.6 | 19 | 100.0 | 5 |
| 65 | NI 1.12 | B- | 2.51719 H | B- | | 875.4 | 6 | 60.0 | 3 |
| 139 | BA 1.89 | B- | 83.06 M 28 | B- | TOT | 889.6 | 19 | 100.0 | 5 |
| 139 | BA 1.36 | B- | 83.06 M 28 | B- | | 913.9 | 19 | 70.0 | 4 |
| 90 | Y 1.99 | B- | 64.10 H 8 | B- | | 933.7 | 12 | 99.9885 | 14 |
| 141 | LA 2.05 | B- | 3.92 H 3 | B- | TOT | 962. | 12 | 100.02 | 22 |
| 141 | LA 2.04 | B- | 3.92 H 3 | B- | | 974. | 12 | 98.14 | 7 |
| 76 | AS 2.27 | B- | 1.0778 D 2 | B- | TOT | 1070.0 | 11 | 100.0 | 3 |
| 93 | Y 2.49 | B- | 10.18 H 8 | B- | TOT | 1167. | 7 | 100.0 | 18 |
| 93 | Y 2.27 | B- | 10.18 H 8 | B- | | 1211. | 6 | 89.6 | 15 |
| 93 | Y 2.49 | B- | 10.18 H 8 | B- | TOT | 1167. | 7 | 100.0 | 18 |
| 93 | Y 2.31 | B- | 10.18 H 8 | B- | | 1211. | 6 | 89.6 | 15 |
| 56 | MN 1.46 | B- | 2.5785 H 6 | B- | | 1216.9 | 5 | 56.3 | 10 |
| 78 | AS 2.68 | B- | 90.7 M 2 | B- | TOT | 1244. | 7 | 101. | 9 |
| 76 | AS 1.38 | B- | 1.0778 D 2 | B- | | 1266.9 | 9 | 51.0 | 20 |
| 87 | KR 2.83 | B- | 76.3 M 6 | B- | TOT | 1333. | 3 | 100. | 4 |
| 112 | AG 3.02 | B- | 3.130 H 9 | B- | TOT | 1354. | 17 | 105. | 6 |
| 42 | K 3.05 | B- | 12.360 H 3 | B- | TOT | 1430.4 | 7 | 100.00 | 13 |
| 92 | Y 3.06 | B- | 3.54 H 1 | B- | TOT | 1436. | 6 | 100.1 | 21 |
| 92 | Y 2.83 | B- | 3.54 H 1 | B- | | 1553. | 5 | 85.7 | 16 |
| 42 | K 2.73 | B- | 12.360 H 3 | B- | | 1565.8 | 6 | 81.90 | 9 |
| 112 | AG 1.94 | B- | 3.130 H 9 | B- | | 1688. | 14 | 54. | 5 |

TABLE 4

| A | ELEMENT | Decay Mode | Half-Life | Rad. Type | | | | Radiation Energy (keV) | | Radiation Intensity (%) | |
|---|---|---|---|---|---|---|---|---|---|---|---|
| 125 | TE 0.0358 | IT | 57.40 D 15 | G | | X | KA1 | 27.47230 | 20 | 61.3 | 23 |
| 125 | I | EC | 59.402 D 1 | G | | X | KA1 | 27.47230 | 20 | 74.3 | 17 |

TABLE 4-continued

| A | ELEMENT | Decay Mode | Half-Life | Rad. Type | | | | Radiation Energy (keV) | | Radiation Intensity (%) | |
|---|---|---|---|---|---|---|---|---|---|---|---|
| | 0.0435 | | | | | | | | | | |
| 93 | MO | EC | 3.5E + 3 Y 7 | G | | | | 30.770 | 20 | 82. | 5 |
| | 0.0537 | | | | | | | | | | |
| 133 | BA | EC | 10.52 Y 13 | G | X | KA1 | | 30.9728 | 3 | 64.9 | 12 |
| | 0.0428 | | | | | | | | | | |
| 145 | SM | EC | 340 D 3 | G | X | KA1 | | 38.7247 | 5 | 71.6 | 12 |
| | 0.0591 | | | | | | | | | | |
| 147 | EU | EC | 24 D 1 | G | X | KA1 | | 40.1181 | 3 | 52. | 3 |
| | 0.0447 | | | | | | | | | | |
| 146 | GD | EC | 48.27 D 10 | G | X | KA2 | | 40.9019 | 3 | 52.2 | 8 |
| | 0.0455 | | | | | | | | | | |
| 146 | GD | EC | 48.27 D 10 | G | X | KA1 | | 41.5422 | 3 | 94.5 | 14 |
| | 0.0836 | | | | | | | | | | |
| 157 | TB | EC | 99 Y 10 | G | X | KA2 | | 42.3089 | 3 | 71. | 6 |
| | 0.0455 | | | | | | | | | | |
| 146 | GD | EC | 48.27 D 10 | G | X | KA1 | | 41.5422 | 3 | 94.5 | 14 |
| | 0.0836 | | | | | | | | | | |
| 157 | TB | EC | 99 Y 10 | G | X | KA2 | | 42.3089 | 3 | 71. | 6 |
| | 0.0644 | | | | | | | | | | |
| 254 | ES | A | 275.5 D 5 | G | | | | 42.60 | 10 | 100.0 | |
| | 0.0907 | | | | | | | | | | |
| 157 | TB | EC | 99 Y 10 | G | X | KA1 | | 42.9962 | 3 | 129. | 10 |
| | 0.118 | | | | | | | | | | |
| 242 | AM | IT | 141 Y 2 | G | | | | 48.63 | 5 | 99.50 | 20 |
| | 0.103 | | | | | | | | | | |
| 157 | TB | EC | 99 Y 10 | G | X | KB | | 48.70 | | 51. | 4 |
| | 0.0528 | | | | | | | | | | |
| 169 | YB | EC | 32.026 D 5 | G | X | KA2 | | 49.7726 | 4 | 53.0 | 10 |
| | 0.0562 | | | | | | | | | | |
| 186 | RE | IT | 2.0E + 5 Y 5 | G | | | | 50. | 37 | 88. | 3 |
| | 0.0936 | | | | | | | | | | |
| 169 | YB | EC | 32.026 D 5 | G | X | KA2 | | 49.7726 | 4 | 53.0 | 10 |
| | 0.0562 | | | | | | | | | | |
| 186 | RE | IT | 2.0E + 5 Y 5 | G | | | | 50. | 37 | 88. | 3 |
| | 0.0936 | | | | | | | | | | |
| 169 | YB | EC | 32.026 D 5 | G | X | KA1 | | 50.7416 | 4 | 93.8 | 18 |
| | 0.101 | | | | | | | | | | |
| 173 | LU | EC | 1.37 Y 1 | G | X | KA1 | | 52.3889 | 5 | 77.2 | 21 |
| | 0.0862 | | | | | | | | | | |
| 172 | HF | EC | 1.87 Y 3 | G | X | KA1 | | 54.0698 | 5 | 64. | 7 |
| | 0.0734 | | | | | | | | | | |
| 177 | LU | B− | 160.4 D 3 | G | X | KA1 | | 55.7902 | 8 | 58.0 | 11 |
| | 0.0690 | | | | | | | | | | |
| 179 | HF | IT | 25.05 D 25 | G | X | KA1 | | 55.7902 | 8 | 56.4 | 19 |
| | 0.0670 | | | | | | | | | | |
| 183 | RE | EC | 70.0 D 11 | G | X | KA1 | | 59.31820 | 10 | 59.9 | 20 |
| | 0.0757 | | | | | | | | | | |
| 44 | TI | EC | 49 Y 3 | G | | | | 67.88 | | 94.4 | 15 |
| | 0.0862 | | | | | | | | | | |
| 172 | HF | EC | 1.87 Y 3 | G | X | KA1 | | 54.0698 | 5 | 64. | 7 |
| | 0.0734 | | | | | | | | | | |
| 177 | LU | B− | 160.4 D 3 | G | X | KA1 | | 55.7902 | 8 | 58.0 | 11 |
| | 0.0690 | | | | | | | | | | |
| 179 | HF | IT | 25.05 D 25 | G | X | KA1 | | 55.7902 | 8 | 56.4 | 19 |
| | 0.0670 | | | | | | | | | | |
| 183 | RE | EC | 70.0 D 11 | G | X | KA1 | | 59.31820 | 10 | 59.9 | 20 |
| | 0.0757 | | | | | | | | | | |
| 44 | TI | EC | 49 Y 3 | G | | | | 67.88 | | 94.4 | 15 |
| | 0.136 | | | | | | | | | | |
| 243 | AM | A | 7370 Y 15 | G | | | | 74.660 | 20 | 68.2 | 14 |
| | 0.108 | | | | | | | | | | |
| 44 | TI | EC | 49 Y 3 | G | | | | 78.34 | | 96.2 | 3 |
| | 0.161 | | | | | | | | | | |
| 178 | HF | IT | 31 Y 3 | G | | | | 88.862 | 6 | 64.4 | 14 |
| | 0.122 | | | | | | | | | | |

Discussion

Work has been performed with intracoronary brachytherapy using Ir$^{192}$ pellets delivered via open ended perfusion catheters to deliver graded doses of radiation to the vessel wall in both the porcine coronary model and the rat carotid model (20–24) While the point definition of the standard dose has varied among investigators (either blood wall interface or an arbitrary point 2 mm from the center of the vessel), it is clear that a dose of 1500 cGy, or greater, delivered from this source to the intima, will prevent neointimal proliferation. Furthermore, the various experiments indicate that the suppression of vascular smooth muscle cell proliferation is durable to at least six months. There was no evidence of myocardial fibrosis or necrosis, as well as no detectable histological abnormalities in surrounding segments of artery. There was also no evidence of pericardial reaction.

The dose fall-off from gamma sources is rapid ($\sim 1/r^{1.5}$), and calculations indicate that at 5 cm from the source the dose would be on the order of 60 cGy, a dose comparable to the dose received by the patient from the fluoroscopy and cineangioraphy. The dose to an operator standing at 100 cm from the source for the duration of the irradiation treatment would be 0.3 cGy per procedure, an unacceptably high dose for the personnel.

Radiation safety considerations suggest that a radioactive source decaying primarily by beta emission would have a more favorable safety profile. This is because the emitted electrons interact strongly with matter leading to almost complete absorption of the emitted energy over very short distances. The distance from the source that is radiated is a function of the energy of the emitted electrons. Calculations indicate that the Emax of the betas should be on the order of 2 MeV in order to have appreciable energy transfer within several millimeters of the source.

Based on these considerations, studies of the effect of beta radiation delivered from a source containing $Sr^{90}/Y^{90}$ by Waksman et al. (25) were undertaken. These investigators studied the ability of this intracoronary beta source to prevent neointimal hyperplasia in the overstretch pig coronary model, and found that doses of radiation between 7 and 56 Gy inhibited neointimal proliferation, at 28 days. A trial, sponsored by Novoste Corp., is currently being pursued using this source.

A number of considerations suggested that another approach to intracoronary radiation with beta emitters be sought. First, with a centrally located wire source, the size of a treatable vessel was significantly limited, because of the rapid attenuation of beta particles in blood. Second, $Sr^{90}$ decays with a half life of 28.74 years to $Y^{90}$. $Y^{90}$ decays with a half life of 64.10 hours, via emission of a high energy beta (Q=2.2815 MeV), to $Zr^{90}$. The latter, Y90, is the active radioisotope for treatment.

The preferred embodiment of this invention uses a radioisotope with similar decay properties, short half life, and desirable chemical properties which could be used as an aqueous source to deliver beta radiation in a balloon catheter.

$^{188}Re$ is a beta-minus emitter with a maximum transition energy of 2.13 MeV, mean beta ray energy of 0.77 MeV, and physical half life of 17 hours. Only 15% of the beta decays are accompanied by 155 keV gamma rays. As seen in the table below, $^{188}Re$ has a beta transition energy almost identical to Y-90, and, from a dosimetric perspective, yields almost identical isodose distributions and dose rate per millicurie activity as Y-90, or Sr-90.

Table of Isotopic Properties

| Isotope | Beta Decay (MeV-Max) | Half-life |
| --- | --- | --- |
| 38-Sr-90 | .55 | 28.8 y |
| 39-Y-90 | 2.28 | 64.1 h |
| 74-W-188 | .35 | 69.4 d |
| 75-Re-188 | 2.12 | 17.0 h |

$^{188}Re$ however has a distinct radiation safety advantage in that it can be chelated to a chemical form, which unlike Y-90, Sr-90, or P-32, is not a bone seeking compound, and is rapidly cleared by the kidneys with a biological half life of approximately 1-3 hours. Because Re is directly below Tc on the atomic table, the chemical properties of these transition metals are similar.

When a liquid $^{188}Re$ solution is used to inflate a balloon catheter, which insures both perfect source centering, and also intimate contact between the radioactive source and the inner arterial wall, radial dose symmetry is assured. Because of this, automatic source centering, and the uniformity of a solution source, the dose as a function of radial distance from the surface of the balloon will also be easily predicable, being a function only of the balloon diameter, and specific activity. For a 3 mm diameter balloon for example, the dose rate at the surface of the balloon (for either Y-90 or Re-188) is approximately 0.14 cGy/sec per mCi/ml (3.78E-11 Gy/sec per Bq/ml), with the dose decreasing to 53% at 0.5 mm. At a specific concentration of 50 mCi/ml ($1.85 \times 10^9$ Bq/ml) one is able to delivery 20 Gy in less than 5 minutes. To allow inflation of a balloon for as long as 5 minutes, a perfusion balloon will be used, such as the ACS Rx Flowtrack, or the SciMed Wave perfusion balloons. The volume of liquid in the balloon is 0.15 ml for a 3.0 mm×2 cm balloon, and an additional 0.10 ml of solution is necessary to fill the inflating lumen in the body of the shaft. Thus the total volume in the perfusion catheter is ~0.25 ml, with a total activity of 12.5 mCi. The balloon will be inflated to nominal pressures necessary to achieve appropriate sizing. All manufacturers currently submit data supporting a rated burst pressure defined as a 95% confidence of 99% maintaining integrity at the rated burst pressure. Thus an upper limit on burst frequency of considerably less than 1% is guaranteed.

Preparation of Rhenium-188-Labeled $MAG_3$ (29-35)

1. Add 2 mg of $SnCl_2-2H_2O$ to a commercial FDA approved $MAG_3$ Kit (TechneScan $MAG_3$® kit, Mallinckrodt Medical) under sterile conditions (Laminar Flow Hood).
2. Add 1 ml of $^{188}Re$ generator eluate to the $MAG_3$ kit as prepared above
3. Heat vial at 100° C. for 60 minutes.
4. Cool solution and filter through sterile Millipore filter before use.

Quality Control

1. Analyze small aliquot of kit preparation by TLC (Merck Si-60 or similar product). After drying, develop plate in acetonitrile. $^{188}Re-MAG_3$ is very polar in this system and remains almost at the origin and any free perrhenate will move to solvent front.
2. A second aliquot is analyzed by TLC by development in saline or water. $^{188}Re-MAG_3$ and any free perrhenate will move to solvent front. Any $^{188}Re$-colloid remains at the origin.
3. A small aliquot of the $^{188}Re-MAG_3$ solution is diluted in 300 μL acetic acid and this solution is then loaded onto a C-18 Sep Pak. The Sep Pak column is previously activated by washing with 2 mL acetonitrile followed by 5 mL of 1% acetic acid solution. After addition of the $^{188}Re-MAG_3$, the column is washed with 3 mL of 1% acetic acid. The $^{188}Re$ activity should remain on the column. The $^{188}Re-MAG_3$ is then eluted with 3 mL of a 50% acetonitrile -50% acetic acid mixture. The Sep Pak column should be sufficiently acidic during this process.

The volumes of $^{188}Re$-perrhenate eluant from the $^{188}W/^{188}Re$ generator and the Sn/citrate solutions can be at least doubled using the contents of one Mallinckrodt $MAG_3$ without significant decrease in the radiolabeling yields.

Data for $^{188}Re-MAG_3$ Preparations

Radiochemical yields are >95% using labeling procedure provided from the Oak Ridge National Laboratory (ORNL) with the use of commercially available kits [i.e., for preparation of $^{99m}Tc-MAG_3$ for imaging renal parenchyma] available from Mallinckrodt, Inc. QC is evaluated using Thin Layer Chromatography to check for free perrhenate and colloids.

| Solvent System | Stationary Phase | Perrhenate$_{Rf}$ | Colloids$_{Rf}$ | ReMAG$_3$ R$_f$ |
|---|---|---|---|---|
| Acetonitrile | Merck Si60 | 1 | 0 | 0 |
| Physiological Saline | Gelman ITLC-SG | 1 | 0 | 1 |

The $^{188}$Re-MAG$_3$ should be used within 3 hours following preparation and QC evaluation, and is suggested that the TLC QC should be evaluated right before use. HAPLY analysis can also be performed. The MAG$_3$ solution should also be filtered through a 0.22 micron Millipore filter before use (36).

Quality Control

ITLC plates are obtained from Gelman Sciences, Ann Arbor, Mich., Product Number 61885, ITLCJ SG, Current Lot=8198. TLC is performed using Silica Gel 60 F254 pre-coated TLC sheets, layer thickness 0.2 mm, from EM Reagents, E. Merck, Darmstadt, Germany.

The rhenium-188-labeled MAG$_3$ agent, the synthesis and QC which are described above, has been evaluated by High Performance Liquid Chromatography (HPLC) and ITLC for periods up to five hours after preparation and no decomposition or effects of radiolysis have been observed. Since the maximum time period between preparation and formulation of $^{188}$Re-MAG$_3$ and administration for intravascular brachytherapy would be 30–60 minutes, these data illustrate the stability for time periods 10–20 times longer than this maximum period.

Stability-$^{188}$Re-MAG$_3$ Stability Study at High Radioactivity Levels $^{188}$Re-MAG$_3$ was prepared using the protocol as described above however using 1 mL generator eluate to dissolve the contents of a commercial MAG$_3$ Kit and addition of 1 mL of SnCl$_2$/citrate solution. The starting activity in 1 ml generator eluate was 1220 Mbq (33 mCi). Thus the concentration of citrate and stannous ions were maintained, however the concentration of the Kit contents in especially the Benzoyl-MAG$_3$ precursor is reduced to half of the original protocol.

The stability was tested using HPLC-chromatography and also TLC as additional control.

Results:

|  | HPLC | TLC |  |
|---|---|---|---|
| End of Synthesis (EOS) | 97.3% | 97.3% |  |
| Time After EOS: |  |  |  |
| 1 hour | 92.0% | ... | 2 hours 91.1%.. |
| 3 hours | 90.3% | ... |  |
| 4 hours | 88.3% | ... |  |
| 5 hours | 100.8% | ... |  |
| 24 hours | 92.4% | 93.4 % |  |

Stability of $^{188}$Re-MAG$_3$ in Presence of Hypaque Contrast Agent $^{188}$Re-MAG$_3$ was prepared as in the upper case starting with an activity of 851 Mbq (23 mCi). After the End of Synthesis, QC via HPLC and TLC, 2 mL of a 50% Triazoate solution was added. Triazoate is known as Hypaque and is the 3,5-Bis(acetylamino)-2,4,6-triiodobenzoic acid sodium salt.

Results:

|  | HPLC | TLC | RP-Sep-Pak |
|---|---|---|---|
| EOS - Before addition of Hypaque: | >95% | 97.6% | 98.3% |
| After mixing with Hypaque: |  |  |  |
| 20 min | >90% | 94.4% | ... |
| 50 min | n.d. | 90.5% | ... |
| 80 min | 86.6% | 87.7% | ... |
| 140 min | 83.3% | 83.3% | ... |

At least 1 hour after mixing a radiochemical purity of >90° is maintained. The only radioactive degradation product found is free perrhenate.

Sterility of Compound

The final $^{188}$Re-MAG$_3$ preparation is filtered through a sterile Millipore filter and checked for sterility and prior to use.

Radioactivity Assay

The rhenium-188 calibration is performed by using secondary standards from ORNL which are calibrated with a Multichannel Analyzer System (HpGe) which is routinely calibrated using a NIST mixed standard obtained from the U.S. Department of Commerce, National Institute of Standards and Technology, SRM-4275C-78 (Sep. 1, 1988).

The radiochemical purity of the $^{188}$Re-MAG$_3$ is assessed and confirmed prior to use by use of ITLC. The rhenium-188 assay is determined using a dose calibrator calibrated using standards calibrated from the NIST standard described above.

Comparison of the Excretion of $^{188}$Re-MAG$_3$ with $^{99m}$Tc-MAG$_3$ in rats Dual Label Excretion Studies of $^{188}$Re-MAG$_3$ and $^{99m}$Tc-MAG$_3$ in Rats

TABLE 5

Excretion kinetics of $^{99m}$Tc-MAG$_3$ in urine of rats

| # | 2 h | 4 h | 6 h | 8 h | 10 h | 12 h | 24 h | 48 h | total |
|---|---|---|---|---|---|---|---|---|---|
| 1 | 74.11 | 5.16 | 2.12 | 2.79 | 1.46 | 1.65 | 4.05 | | 91.35 |
| 2 | 34.58 | 15.88 | 0 | 2.30 | 1.14 | 0.94 | 5.66 | | 60.50 |
| 3 | 48.08 | 9.37 | 0.04 | 5.65 | 0.70 | 0 | 9.28 | | 73.12 |
| 4 | 59.54 | 10.12 | 2.75 | 0.98 | 1.40 | 1.59 | 2.08 | | 78.46 |
| mean ± s.d. | 54.08 ± 16.80 | 10.13 ± 4.41 | 1.22 ± 1.42 | 2.93 ± 1.96 | 1.18 ± 0.35 | 1.05 ± 0.77 | 5.26 ± 3.05 | | 75.86 ± 12.78 |

TABLE 6

Excretion kinetics of $^{99m}$Tc-MAG$_3$ in feces of rats

| # | 2 h | 4 h | 6 h | 8 h | 10 h | 12 h | 24 h | 48 h | Total |
|---|---|---|---|---|---|---|---|---|---|
| 1 | 0.02 | 0 | 0 | 0.02 | 0.36 | 0.93 | 5.28 | | 6.61 |
| 2 | 1.23 | 0 | 0 | 0 | 3.22 | 0.92 | 6.27 | | 11.64 |
| 3 | 0.04 | 0 | 0 | 1.18 | 1.55 | 0 | 4.33 | | 7.10 |
| 4 | 0 | 0 | 0.01 | 0.05 | 1.50 | 2.04 | 3.31 | | 6.91 |
| mean ± s.d. | | | | | 8.06 | 2.39 | | | 8.06 ± 2.39 |

TABLE 7

Excretion kinetics of $^{188}$Re-MAG$_3$ in urine of rats

| # | 2 h | 4 h | 6 h | 8 h | 10 h | 12 h | 24 h | 48 h | Total |
|---|---|---|---|---|---|---|---|---|---|
| 1 | 82.55 | 5.14 | 1.73 | 3.39 | 1.50 | 1.34 | 3.76 | 1.89 | 101.25 |
| 2 | 39.22 | 15.42 | 0 | 2.03 | 1.08 | 0.70 | 5.17 | 2.39 | 66.01 |
| 3 | 51.95 | 8.14 | 0 | 4.82 | 0.67 | 0 | 9.67 | 2.31 | 77.56 |
| 4 | 64.80 | 10.58 | 2.16 | 0.75 | 1.36 | 1.29 | 1.68 | 0.44 | 83.06 |
| mean ± S.D. | 59.63 ± 18.51 | 9.82 ± 4.35 | 0.97 ± 1.14 | 2.75 ± 1.75 | 1.15 ± 0.37 | 0.83 ± 0.63 | 5.07 ± 3.39 | 1.76 ± 0.9 | 81.97 ± 14.69 |

TABLE 8

Excretion kinetics of $^{188}$Re-MAG$_3$ in feces of rats

| # | 2 h | 4 h | 6 h | 8 h | 10 h | 12 h | 24 h | 48 h | Total |
|---|---|---|---|---|---|---|---|---|---|
| 1 | 0.03 | 0 | 0 | 0.02 | 0.41 | 1.17 | 5.86 | 0.85 | 8.34 |
| 2 | 1.50 | 0 | 0 | 0 | 3.79 | 1.09 | 6.46 | 2.26 | 15.1 |
| 3 | 0.03 | 0 | 0 | 1.30 | 1.79 | 0 | 4.47 | 0.52 | 8.08 |
| 4 | 0.01 | 0 | 0 | 0.04 | 1.67 | 2.24 | 3.46 | 0.70 | 8.12 |
| mean ± S.D. | | | | | | | | | 9.91 ± 3.46 |

TABLE 9

Radionuclide Ratios

| Sample | Time of Measurement | Count Ratio of 140 keV/155 keV | Ratio After Correction for Physical Decay of the Individual Radioisotopes |
|---|---|---|---|
| aliquot | 10:10 | 31.8 | — |
| std. rat #1 | 10:14 | 31.3 | — |
| std. rat #2 | 10:22 | 31.7 | — |

TABLE 9-continued

Radionuclide Ratios

| Sample | Time of Measurement | Count Ratio of 140 keV/155 keV | Ratio After Correction for Physical Decay of the Individual Radioisotopes |
|---|---|---|---|
| urine of rat 1, 2 hours | 12:49 | 22.7 | 27.8 |

TABLE 9-continued

Radionuclide Ratios

| Sample | Time of Measurement | Count Ratio of 140 keV/155 keV | Ratio After Correction for Physical Decay of the Individual Radioisotopes |
|---|---|---|---|
| urine of rat 1, 4 hours | 17:39 | 17.2 | 30.0 |

Biodistribution Data for $^{99m}$Tc-MAG$_3$ and $^{188}$Re-MAG$_3$ in a dual label study

TABLE 10

Biodistribution Data for $^{99m}$Tc-MAG$_3$ (% inj. dose/g tissue ± standard deviation) in rats following tail vein injections.

| organ | 2 h | 6 h | 24 h |
|---|---|---|---|
| blood | 0.18 ± 0.02 | 0.13 ± 0.00 | 0.05 ± 0.00 |
| liver | 0.15 ± 0.02 | 0.15 ± 0.00 | 0.11 ± 0.01 |
| kidneys | 0.61 ± 0.11 | 0.43 ± 0.09 | 0.40 ± 0.11 |
| heart | 0.09 ± 0.02 | 0.08 ± 0.01 | 0.04 ± 0.00 |
| lung | 0.15 ± 0.04 | 0.07 ± 0.02 | 0.04 ± 0.03 |

TABLE 10-continued

Biodistribution Data for $^{99m}$Tc-MAG$_3$ (% inj. dose/g tissue ± standard deviation) in rats following tail vein injections.

| organ | 2 h | 6 h | 24 h |
|---|---|---|---|
| thyroid | 2.41 ± 0.95 | 2.43 ± 0.24 | 0.76 ± 0.59 |
| small intestine | 0.12 ± 0.04 | 0.07 ± 0.01 | 0.03 ± 0.00 |
| large intestine | 0.14 ± 0.02 | 0.18 ± 0.00 | 0.06 ± 0.00 |
| contents of l.i. | 0.72 ± 0.18 | 1.16 ± 0.23 | 0.05 ± 0.01 |
| contents of s.i. | 1.84 ± 2.27 | 0.08 ± 0.03 | 0.02 ± 0.01 |
| spleen | 0.06 ± 0.02 | 0.07 ± 0.01 | 0.06 ± 0.00 |
| bone | 0.05 ± 0.02 | 0.03 ± 0.03 | 0.02 ± 0.01 |

TABLE 11

Biodistribution of $^{188}$Re-MAG$_3$ (% inj. dose/g tissue ± standard deviation) in rats following tail vein injections.

| organ | 2 h | 6 h | 24 h |
|---|---|---|---|
| blood | 0.07 ± 0.01 | 0.08 ± 0.02 | 0.05 ± 0.02 |
| liver | 0.03 ± 0.01 | 0.03 ± 0.00 | 0.02 ± 0.00 |
| kidneys | 0.12 ± 0.03 | 0.11 ± 0.02 | 0.07 ± 0.01 |
| heart | 0.02 ± 0.03 | 0.00 ± 0.00 | 0.01 ± 0.00 |
| lung | 0.05 ± 0.02 | 0.02 ± 0.00 | 0.01 ± 0.01 |
| thyroid | 0.70 ± 0.49 | 0.76 ± 0.42 | 0.74 ± 0.76 |
| s. intestine | 0.06 ± 0.04 | 0.01 ± 0.00 | 0.01 ± 0.00 |
| l. intestine | 0.06 ± 0.02 | 0.13 ± 0.03 | 0.02 ± 0.00 |
| contents of l.i. | 0.87 ± 0.32 | 1.42 ± 0.33 | 0.05 ± 0.01 |
| contents of s.i. | 1.97 ± 2.58 | 0.06 ± 0.05 | 0.02 ± 0.01 |
| spleen | 0.03 ± 0.02 | 0.00 ± 0.01 | 0.02 ± 0.01 |
| bone | 0.09 ± 0.11 | 0.01 ± 0.01 | 0.04 ± 0.05 |

Conclusion

The above data shows that the ratio of Tc and Re only vary within a relative small range. This supports clearly that both radionuclides are handled similarly in vivo in the rat. Thus using the rat 1, 2 hours value as a standard for the calculations as described above is consistent with this observation.

Preclinical Pharmacology/Toxicology

Direct radiation with beta sources of comparable energy (Sr90/Y90) as high as 5600 cGy caused no short term toxicity (14 days) in pig coronary arteries (21). Information concerning the toxicity of ReMAG$_3$ is limited. However, given the carrier-free state of the Re-188 used in these experiments, the maximal mass of injected Re is less than 1 ng. Another Re isotope, Re-186, also a beta emitter, has been conjugated to a monoclonal antibody via the MAG$_3$ chelator, and has been used by injection in Phase I/II therapeutic studies. Fourteen patients have been treated with doses of 300 mCi/m$^2$; the only noted toxicity is referable to bone marrow suppression by the isotope. These doses are ~40 times the maximal releasable dose in this study. Furthermore, the mass of released rhenium is even greater, given the carrier-free state of Re-188. According to NeoRx information patient doses of Re would be on the order of micrograms, suggesting even greater pharmacological safety. The risk from unconjugated MAG$_3$ is negligible, given its widespread use as chelator of Tc-99m.

As alluded to previously, the probability of balloon rupture at nominal balloon inflation pressures are substantially less than one percent. Animal experiments and calculations of the individual organ dose received by a $^{188}$Re-MAG$_3$ release have been done. Because the isotope is in solution, there would be no significant local arterial deposition. In fact, attempts to intentionally deposit soluble compounds in vessel walls for their pharmacological properties have been notoriously poor. The distribution and elimination of simultaneously injected $^{99m}$Tc-MAG$_3$ and $^{188}$Re-MAG$_3$ in rats are identical. Based upon these findings Dr. Michael Stabin of the Oak Ridge Institute for Science and Education (ORISE) has calculated, based on the MIRD formalism, the individual organ dose of released $^{188}$Re-MAG$_3$. The results of these. calculations are shown in Tables 10 and 11 above. The only organ receiving a dose of greater than 5 cGy would be the urinary bladder wall. This assumes spontaneous urination every 4–6 hours. The dose is substantially reduced if the radioactive urine is drained more frequently. If a bladder catheter is placed and there is continual urinary drainage after release of the isotope, there is a decrease of dose by greater than five fold. Thus, release of the isotope upon balloon rupture would necessitate placing a bladder catheter until the urinary counts excreted return to background. Based on animal data, and on human $^{99m}$Tc-MAG$_3$ distribution this should occur in less than 12 hours.

Dosimetry

Presented below are experimental measurements and analytical calculations for a $^{90}$Y-chloride-filled balloon which may be suitable for use in endocardia brachytherapy. Similar calculations can be performed to determine the requisite concentration of a chelated radionuclide in solution in a balloon catheter for delivery of a desired radiation dosage to the tissue of the luminal structure.

Materials and Methods

Doses of 15–20 gray are required to a length of 2–3 cm of the arterial wall, which is 2–4 mm in diameter. The dose distribution must be confined to the region of the angioplasty with minimal dose to normal vessels and myocardium. Dose rates >5 gray/min would be optimal in order to limit treatment times are highly desirable as any source or catheter inserted in the artery restricts blood flow and increases the risk of myocardial complication and thrombosis.

Several high-energy beta-minus emitters, such as $^{90}$Y and $^{186}$Re, are available in liquid form and appear to be promising as filling agents for a radioactive balloon. Both isotopes can be obtained from parent-daughter generators at very high specific activities. They could, therefore, be produced locally and economically. Other isotopes, such as $^{166}$Ho, and $^{42}$K, produced via neutron or proton activation may also prove feasible(41, 42).

Calculations $^{90}$Y is a pure beta-minus emitter with a half-life of 64 h and transition energy of 2.27 MeV. It can be produced by neutron activation of $^{89}$y, or more commonly, from the decay of $^{90}$Sr which is also a pure beta emitter with half-life of 28 years and transition energy of 0.54 MeV. For the experiments reported here $^{90}$Y was obtained in the form of yttrium-chloride solution cluted from a $^{90}$Sr generator with hydro-cloric acid. Specific concentrations >80 mCi/ml (2.96×10$^9$ Bq/ml) can readily be obtained (Nordion International, Ottawa, Canada). $^{90}$Sr concentration is less than 20 pCi per curie of yttrium (0.002%).

Dose (in gray) per decay versus radial distance (in cm) from a point source can be calculated from first principle (43) using the equation:

$$\text{Dose}(r) = \int_{E_{min}}^{E_{max}} F(E) * C * S(E') * dE / 4\Pi r^2 \qquad \text{Eq. 4}$$

where r=distance(cm), F(E)dE=number of electrons emitted per decay in the energy interval (E+dE) MeV, C=units conversion factor of 1.6E-10 Gy g/MeV, S(E')=restricted collision stopping power for electron of energy E' (MeV/cm), E'=energy at distance r from the source of electron with initial energy E, p=density(g/cm$^3$), $E_{min}$=minimum energy of electron with range greater than or equal to r, $E_{max}$= maximum energy of electron as defined by the beta decay transition energy.

Electron ranges and stopping powers based on the continuous slowing down approximation (CSDA) are given by Berger and Seltzer (44) and F(E) spectra are known(45, 46). Dose calculations based on stopping power tables derived from the CSDA however may introduce errors due to range straggling and Landau energy loss straggling. A more accurate solution of Eq. 4 via Monte Carlo calculations for several common isotopes has been presented in the form of dose kernel functions (which give directly the dose per beta decay as a function of radial distance) by Simpkin and Mackie (46).

The dose rate (Gy/s at a point P(x',y',z') resulting from a radioactive-filled balloon can be determined by numerical integration of the dose kernel over the volume of the balloon as given by Eq. 5:

$$\text{Dose rate } (p) = \int k(r')^* (A/V)^* dV \quad \text{Eq. 5}$$

where k(r)=dose kernel=Gy/decay, $r' = cm = [(x'-x)^2 + (y' - r^*\sin\Theta)^2 + (z' - r^*\cos\Theta)^2]^{1/2}$, A/V=activity per unit volume ($Bq/cm^3$), $dV = r^* dr^* de^* dx$, and the integration is performed over $-L/2 < x < l/2$, $r_i < r < r_0$, and $0 < \Theta < 2\Pi$.

Experimental

Gaf-chromic film is used for dosimetric measurements, particularly for brachy-therapy sources. It is nearly tissue equivalent (TE) with near linear response (i.e. optical density (OD) verses dose), requires no post-irradiation processing, and has a large dynamic range (OD increases from approximately 0.1 to 3.0 for doses between 0 and 200 gray).

A TE phantom was constructed in the form of a 5-cm-diam cylinder and cut in half radially to permit insertion of a slice of GAF-chromic film. Both the phantom and the film had central holes 3 mm in diam, drilled axially to permit insertion and inflation of the balloon dilitation catheter. Films exposed in this phantom permit determination of the dose distribution around the balloon, at the site of the angioplasty.

A second phantom was made, identical to the first except the axial hole was 1 mm in diameter instead of 3 mm, to match the diameter of the longer shaft section of catheter which contains tubes for inflating the balloon and also the guide wire. This phantom was used for determination of the dose to the formal and iliac arteries.

Both phantoms were assembled with the GAF-chromic film in place. The dilitation catheter balloon (Mansfield/Boston Scientific, Watertown, Mass.) was 3 mm in diameter by 2 cm in length with a 4 atm nominal inflation pressure (15 atmosphere rated burst pressure). The central channel was designed for a 0.46 mm guide wire. The balloon was filled with 14 mCi/ml ($5.18 \times 10^8$ Bq/ml)$^{90}$Y-chloride solution to a pressure of 4 atm, resulting in full inflation of the balloon. A total of 1-ml radioactive solution was required to fill the balloon, catheter shaft, pressure syringe, and lure-lock connectors (i.e., three-way stop c). The volume of the balloon itself however is only 0.14 ml, with an additional 0.1 ml (approximately) required to fill the catheter shaft, making a total of 0.24 ml inside the patient. The majority of the radioactive liquid remains in the luer-lock connectors.

Several film exposures were made with irradiation times ranging from 5–18 h in order to obtain films in the 0.1–3 OD range. First, isodose distributions in the radial place were measured by placing the balloon inside a hole of 3-mm diameter cut through the film and the phantom. The phantom was also sliced axially enabling a second set of exposures in which the films were placed adjacent to and parallel to the long axis of the balloon, thus permitting measurement of the axial dose distribution. Calibration (i.e. H and D) curves for the film were obtained by exposing films to doses of 6–200 gray with a calibrated cobalt-60 teletherapy source. Differences in film response between gamma rays and electrons have been reported to be less than 3% (47).

All exposed films were analyzed with a 12-bit He-Ne laser scanner with spatial resolution of 0.1 mm. Optical densities were converted to dose based on the H and D curve and compared to calculations from Eq.(5).

Results

The measure H and D curve for $^6$Co was found to be linear up to doses of 200 Gy (corresponding OD of approximately 3.0). Agreement between measured and calculated radial doses around the balloon is 6% for distance between 2.5 and 5.0 mm from the center of the catheter (i.e., 1,0–3.5 mm from the surface of the balloon).

Measurement uncertainties include 2% in source calibration (obtained from the manufacturer), 5% in dilution errors, and 3% in film calibration. Uncertainties in calculated doses arise almost entirely from errors in the kernel functions, which are difficult to estimate. The kernel functions of Simpkin and Mackie (46) used here however, differ from those given by Berger (48) by approximately 5% at radial distances <1.5 mm or >5.0 mm. One may therefore take 5% as an approximate uncertainty in the calculated dose values. The 6% agreement between our measured and calculated doses is thus well within the estimated uncertainties.

Also, the fact that the dose around the shaft of the catheter is 10–100 times lower than the dose around the balloon, meaning that in a clinical situation the dose to any vessel other than the area prescribed for treatment would be negligible.

Air bubbles occasionally get into the balloon in spite of careful efforts to aspriate the balloon, and fully fill with liquid. The dose immediately adjacent to such a bubble is seen to be 30% lower than for a filled balloon. It is easily demonstrable via calculations that on the side of the balloon opposite the air bubble, the dose is within 1%–2% of a fully filled balloon. Thus even with the presence of a small air bubble, the dose uniformity around a liquid-filled balloon is superior to a solid wire or seed.

As seen previously, in the radial plane, dose in the axial plane also shown a 20%–30%. decrease in dose near the bubble, with good dose uniformity elsewhere, and rapid dose fall-off at distances beyond the ends of the balloon. These data, combined with the radial isodose distributions demonstrate that a radionuclide filled balloon yields an extremely uniform dose distribution with rapid dose fall-off beyond the treatment volume.

Isotopes with short physical half-lives (on the order of 0.25–20 h) can most readily be produced locally from radio-active generators. The $^{90}$Sr-$^{90}$Y is one such possibility, but other such as $^{42}$Ar— $^{42}$K, $^{144}$Ce— $^{144}$Pr, and $^{188}$W— $^{188}$Re, are known. Positron emitters instead of beta-minus emitters can also be used because positron emitters have the same dosimetric characteristics as beta-minus emitters.

The practicality of any particular isotope will depend on the relationship between its half-life, availability, cost and excretion characteristics when in a complex with a chelating agent.

References

1. Chokshi SK, Meyers S, Abi-Mansour P. Percutaneous transluminal coronary angioplasty: ten years' experience, Prog Cardiovasc Dis 1987, 30: 147–210.
2. Leimgruber PP, Roubin GS, Hollman J, Restenosis after successful coronary angioplasty in patients with single-vessel disease, Circulation 1986, 73: 710–17.
3. Mabin TA, Holmes DR, Smith HC, Follow-up clinical results in patients undergoing percutaneous transluminal coronary angioplasty, Circulation 1985, 71: 754–60.
4. Holmes DR Jr., Vliestra RE, Smith HC, Restenosis after percutaneous transluminal coronary angioplasty (PTCA): a report from the PTCA registry of the National Heart, Lung, and Blood Institute, Am J Cardiol 1984, 53: 77C–81C.

5. Califf RM, Fortin DF,Frid DJ, Restenosis after coronary angioplasty: An overview, JACC 1991,17: 2–13B.
6. Austin GE, Ratliff NB, Hollman J, Tabei S, Phillips DF., Intimal proliferation of smooth muscle cells as an explanation for recurrent coronary artery stenosis after percutaneous transluminal coronary angioplasty, JACC 1985, 6: 369–75.
7. Clowes AW, Schwartz SM, Significance of quiescent smooth muscle migration in the injured rat carotid artery, Circ Res 1985, 56: 139–45.
8. Liu MW, Roubin GS, King SB III, Restenosis after coronary angioplasty: Potential biological determinants and role of intimal hyperplasia, Circulation 1989, 79: 1374–87.
9. Steele PM, Chesebro JH, Stanson AW, Balloon angioplasty: natural history of the pathophysiological response to injury in a pig model, Circ Res 1985, 57: 105–12.
10. Barnathan ES, Schwartz JS, Taylor L, Laskey WK, Kleaveland JP, Kussmaul WG, Hirshfeld JW Jr., Aspirin and dipyridamole in the prevention of acute coronary thrombosis complicating coronary angioplasty, Circulation 1987, 76:125–34.
11. Thornton MA, Gruentzig AR, Hollman J, King SB, Douglas JS, Coumadin and aspirin in the prevention of recurrence after transluminal coronary angioplasty: a randomized study, Circulation 1984, 69:721–7.
12. Whitworth HB, Roubin GS, Hollman J, Meier B, Leimgruber PP, Douglas JS Jr, King SB III, Gruentzig AR, Effect of nifedipine on recurrent stenosis after percutaneous transluminal coronary angioplasty, JACC 1986, 8:1271–6.
13. Serruys PW, Strauss BH, Beatt KJ, Bertrand ME, Duel J, Rickards AF, Meier B, Goy JJ, Vogt P, Kappenberger L, Angiographic follow-up after placement of a self-expanding coronary-artery stent, N Engl J Med 1991, 324:13–17.
14. US Directional Coronary Atherectomy Investigator Group: Restenosis following directional coronary atherectomy in a multicenter experience. Circulation 1990, 82(suppl III): III-679.
15. Muller DW, Ellis SG, Topol EJ, Experimental models of coronary artery restenosis, JACC 1992, 19:418–32.
16. Popma JJ, Califf RM, Topol EJ, Clinical trials of restenosis after coronary angioplasty, Circulation 1991, 84:1426–36.
17. Muller DW, Ellis SG, Topol EJ, Colchicine and antineoplastic therapy for the prevention of restenosis after percutaneous coronary interventions, JACC 1991, 12(6 Suppl B): 126B–131B.
18. Knudtson ML, Flintoft VF, Roth DL, Hansen JL, Duff HJ, Effect of short-term prostacyclin administration on restenosis after percutaneous transluminal coronary angioplasty, JACC 1990, 15: 691–97.
19. Hermans WRM, Rensing BJ, Strauss BH, Serruys PW. Prevention of restenosis after percutaneous transluminal coronary angioplasty: The search for a "magic bullet" Am Heart J 1991, 122: 171–87.
20. Waksman, R, Robinson, KA, Croaker, IR, Gravanis, MB, Palmer, SJ, Wang, C, Cipolla, GD, and King, S, Intracoronary radiation before stent implantation inhibits neointima formation in stented porcine coronary arteries, Circulation, 1995, 92(6): p. 1383–6.
21. Waksman, R, Robinson, KA, Croaker, IR, Gravanis, MB, Cipolla, GD, and King, S, Endovascular low-dose irradiation inhibits neointima formation after coronary artery balloon injury in swine. A possible role for radiation therapy in restenosis prevention, Circulation, 1995, 91(5): p. 1533–9.
22. Wiedermann, JG, Marboe, C, Amols, H, Schwartz, A, and Weinberger, J, Intracoronary irradiation markedly reduces neointimal proliferation after balloon angioplasty in swine: persistent benefit at 6-month follow-up, Journal of the American College of Cardiology, 1995. 25(6): p. 1451–6.
23. Shimotakahara, S and Mayberg, MR, Gamma irradiation inhibits neointimal hyperplasia in rats after arterial injury, Stroke, 1994, 25(2): p. 424–8.
24. Wiedermann, JG, Marboe, C, Amols, H, Schwartz, A, and Weinberger, J, Intracoronary irradiation markedly reduces restenosis after balloon angioplasty in a porcine model. Journal of the American College of Cardiology, 1994, 23(6): p. 1491–8.
25. Waksman, R, Robinson, KA, Croaker, IR, Wang, C, Gravanis, MB, Cipolla, GD, Hillstead, RA, and King, SB, Intracoronary low-dose b-radiation inhibits neointima formation after balloon injury in the swine restenosis model, Circulation, 1995, 92(10): p. 3025–31.
26. Popowski, Y, Verin, V, Papirov, I, Nouet, P, Rouzaud, M, Grob, E, Schwager, M, Urban, P, Rutishauser, W, & Kurtz, JM, High dose rate brachytherapy for prevention of restenosis after percutaneous transluminal coronary angioplasty: preliminary dosimetric tests of a new source presentation, International Journal of Radiation Oncology, Biology, Physics, (1995) 33(1), 211–5.
27. Verin, V, Popowski, Y, Urban, P, Belenger, J, Redard, M, Costa, M, Widmer, MC, Rouzaud, M, Nouet, P, Grob, E, Intra-arterial beta irradiation prevents neointimal hyperplasia in a hypercholesterolemic rabbit restenosis model. Circulation, (1995) 92(8), 2284–90.
28. Order, SE, and Donaldson, SS Radiation Therapy of Benign Diseases. Berlin; New York : Springer-Verlag, c1990.
29. Van Gog FB, Visser GWM, Klok R, Van der Schors R, Snow GB, van Dongen GAMS, "Monoclonal Antibodies Labeled with Rhenium-186 using the MAG3 Chelate: Relationship between the Number of Chelated Groups and Biodistribution Characteristics," J. Nucl. Med (1996) 37:352–362.
30. Visser GW, Gerretsen M, Herscheid JD, Snow GS, van Dongen G, "Labeling of Monoclonal Antibodies with Rhenium-186 Using the $MAG_3$ Chelate for Radioimmunotherapy of Cancer: A Technical Protocol," J. Nucl. Med. (1993) 34:1953–1963.
31. Hanso, L, Taylor, A, Jr., Marzilli, LG, "Structural Characterization of the rhenium (V) Oxo Complex of Mercaptoacetyltriglycine in its Dianionic Form," Metal Based Drugs (1995)2:105–110.
32. Rao, Adhikesavlu, Camerman, Fritzberg, "Synthesis and Characterization of Monooxorhemium (V) Complexes of Mercaptoacetylglycyl-glycylgycine. Crystal Structure of Tetrabutyylammonium oxO (mercaptoacetyl-glycylglycylglycine)rhenate (V)," Inorganica Chimica Acta (1991) 180:63–67.
33. Guhlke, S, Diekmann, D., Zamora, P, Knapp,FF Jr. and Biersack, HJ $MAG_3$ p-Nitrophenyl Ester for Tc-99m and Re-188 Labeling of Amines and Peptides (1995).
34. Nicolini, N, Bandoli, G, and Mazzi, U. (editors), Technetium and Rhenium in Chemistry and Nuclear Medicine, 4, Editorali, Padua, Italy, pp. 363–366.
35. Zamora P. O., Guhlke S., Bender H., Diekmann D., Rhodes B. A., Biersack H.-J., Knapp F. F. (Russ) (1996); Experimental Radiotherapy of Receptor-Positive Human Prostate Adenocarcinoma with 188Re-RC-160, a Directly-Radiolabeled Somatostatin Analogue. Int. J. Cancer 65, 1–8.

36. Gellman, J., Healey G., Qingsheng, C., Tselentakis, M. J. The effects of very low dose irradiation on restenosis following balloon angioplasty. A study in the atherosclerotic rabbit. *Circulation* 84, Supple 11, 46A59A (1991).
37. Mayberg, M. R., Luo, Z., London, S., Gajdusek, C., Rasey, J. S. Radiation inhibition of intimal hyperplasia after arterial injury. *Rad. Res.* 142, 212–220 (1995)
38. Prestwich, W. V., Kennet, T. J., and Kus, F. W. The dose distribution produced by a $P^{32}$-coated stent. *Med. Phys.* 22, 313–320 (1995).
39. Schwartz, R. S., Koval, T. M., Edwards, W. D., Camrud, A. R., Bailey, K. R., Brown, K., Vlietstra, R. E., and Holmes, D. R. Effect of external beam irradiation on neointimal hyperplasia after experimental coronary artery injury. *J. Am. Col. Cardiol.* 19, 1106–1113 (1992).
40. Wiederman, J., Leavy, J., Amols, H., Schwartz, A., Homma, S., Marobe, C., and Weinberger, J. Effects of high dose intracoronary irradiation on vasomotor function and smooth muscle histopathology. *Am. J. Phys. (Heart and Circ. Physiol.)* 267, H125–H132 (1994).
41. Spencer, R. P., Nuclear medicine and therapy: a reorientation to specificity and beta ray generators, Symposium on Therapy in Nuclear Medicine, 3–15, (1978).
42. Knapp, F. F., Callahan, A. P., Beets, A. L., Mirxadeh, S., and Hsieh, B. T., Processing of reactor-produced $^{188}W$ for fabrication of clinical scale alumina-based $^{188}W/^{188}Re$ generators, Appl. Radiat. Isot., 45:1123–1128 (1994).
43. Johns, H. E., and Cunningham, J. R. The Physics of Radiology (4th Edition). Charles Thomas, Publisher (Springfield, Ill., 1983).
44. Berger, M. J. and Seltzer, S. M., Stopping powers and ranges of electrons and positrons, 2nd ed., U.S. Dept. Of Commerce Publications NBSIR 82-2550-A, (1983).
45. Friedell, H. L., Thomas, C. I., and Krohmer, J. S. Description of an $Sr^{90}$ beta-ray applicator and its use on the eye. *Amer. J. Roentq.* 65, 232–245 (1951).
46. Simpkin, D. J. and Mackie, T. R., EGS Monte Carlo determination of the beta dose kernel in water, Med. Phys., 17:179–186 (1990).
47. McLaughlin, W. L, Chen. Y. D, Soares, C. G., Miller, A., VanDyck, G., and Lewis, D. F., Sensitometry of the response of a new radiochromic film dosimeter to gamma radiation and electron beams, Nucl. Instrum. Meth. Phys. Res., A 302:165–176 (1991).
48. Berger, M. J., Distribution of absorbed dose around point sources of electrons and beta particles in water and other media, MIRD Pamphlet No. 7, J. Nucl. Med. 12, Suppl. NO. 5, 5–24 (1971).
49. Bottcher, H. D., Schopohl, B., Liermann, D., Kollath, J., and Adamietz, I. A. Endovascular irradiation-a new method to avoid recurrent stenosis after stent implantation in peripheral arteries: technique and preliminary results. *Int. J. Rad. Onc. Biol. Phys.* 29, 183–186 (1994).
50. MIRD. Method of calculation: "S", absorbed dose per unit cumulated activity for selected radionuclides and organs. *MIRD Pamphlet* #11 (1975).
51. Nath, R., Anderson, L., Luxton, G., et. al. Dosimetry of interstitial brachytherapy sources: recommendations of the AAPM radiation therapy committee task group No. 43. *Med. Phys.* 22, 209–234 (1995).
52. Prestwich, W. V., Kennet, T. J., and Kus, F. W. The dose distribution produced by a $P^{32}$-coated stent. *Med. Phys.* 22, 313–320 (1995).
53. Williamson, J. F., and Zuofend, L. Monte carlo aided dosimetry of the microselectron pulsed and high dose-rate $^{192}Ir$ sources. *Med. Phys.* 22, 809–819 (1995)

What is claimed is:

1. A method of inhibiting a disease process in a luminal structure of a subject comprising introducing within the luminal structure a complex of a radionuclide and a chelating agent, said complex being introduced in an amount effective to inhibit the disease process and said chelating agent of said complex controlling the biodistribution of the complex in the subject.
2. The method of claim 1, wherein the subject is a mammal.
3. The method of claim 2, wherein the subject is a human.
4. The method of claim 1, wherein the radionuclide is $^{188}Re$.
5. The method of claim 1, wherein the chelating agent is $MAG_3$.
6. The method of claim 1, wherein the complex is a $^{188}Re$-$MAG_3$ complex.
7. The method of claim 1, wherein the complex is introduced within the luminal structure through a catheter in the luminal structure.
8. The method of claim 7, wherein the catheter is a balloon catheter.
9. The method of claim 1, wherein the disease process is restenosis.
10. The method of claim 1, wherein the disease process is cell proliferation.
11. The method of claim 10, wherein the cell proliferation is associated with an endobronchial, bile duct, gastrointestinal, cervical, urinary bladder, or endometrial tumor.
12. The method of claim 1, wherein the luminal structure is an artery.
13. The method of claim 1, wherein the luminal structure is a vein, a bypass graft prosthesis, a portion of the gastrointestinal tract, a portion of the biliary tract, a portion of the genitourinary tract, or a portion of the respiratory tract.
14. The method of claim 1, wherein said radionuclide is Na-24, Si-31, K-42, Sc-44, Co-55, Cu-61, Ga-66, Ga-68, Ga-72, Se-73, Sr-75, Br-76, Kr-77, Ge-77, Sr-90, Y-90, Tc-99, Tc-99m, Pd-103, In-110, Sb-122, I-125, Ho-166, Re-186, Ir-192, or Bi-212.
15. An apparatus for treating a disease process in a luminal structure of a subject comprising:
 a balloon catheter with a fluid delivery port connected thereto for insertion and removal of fluid, said balloon catheter having a size sufficiently small to be received in a luminal structure of a subject; and
 a radioactive fluid in the balloon catheter, said radioactive fluid comprising a complex of a radionuclide and a chelating agent, said complex being present in an amount effective to inhibit the disease process and said chelating agent of said complex being present in an amount effective for controlling the biodistribution of the complex in the subject in the event that at least some of the complex escapes the balloon catheter.
16. The apparatus of claim 15, wherein the radionuclide is $^{188}Re$.
17. The apparatus of claim 15, wherein said radionuclide is Na-24, Si-31, K-42, Sc-44, Co-55, Cu-61, Ga-66, Ga-68, Ga-72, Se-73, Sr-75, Br-76, Kr-77, Ge-77, Sr-90, Y-90, Tc-99, Tc-99m, Pd-103, In-110, Sb-122, I-125, Ho-166, Re-186, Ir-192, or Bi-212.
18. The apparatus of claim 15, wherein the chelating agent is $MAG_3$.
19. The apparatus of claim 15, wherein the complex is a $^{188}Re$-$Mag_3$ complex.
20. A method of treating a disease process in a luminal structure of a subject comprising introducing within the luminal structure the apparatus of claim 15.
21. The method of claim 20, wherein the disease process is restenosis.

22. The method of claim 20, wherein the disease process is cell proliferation.

23. The method of claim 22, wherein the cell proliferation is associated with an endobronchial, bile duct, gastrointestinal, cervical, or endometrial tumor.

24. The method of claim 20, wherein the luminal structure is an artery.

25. The method of claim 20, wherein the luminal structure is a vein, a bypass graft prosthesis, a portion of the gastrointestinal tract, a portion of the biliary tract, a portion of the genitourinary tract, or a portion of the respiratory tract.

* * * * *